(12) United States Patent
Uthgenannt et al.

(10) Patent No.: US 8,407,067 B2
(45) Date of Patent: *Mar. 26, 2013

(54) METHOD AND APPARATUS FOR MANUFACTURING AN IMPLANT

(75) Inventors: Brian A. Uthgenannt, Winona Lake, IN (US); Robert Metzger, Wakarusa, IN (US); Nathan E. Belcher, Warsaw, IN (US); Joshua B. Catanzarite, Warsaw, IN (US)

(73) Assignee: Biomet Manufacturing Corp., Warsaw, IN (US)

( * ) Notice: Subject to any disclaimer, the term of this patent is extended or adjusted under 35 U.S.C. 154(b) by 89 days.

This patent is subject to a terminal disclaimer.

(21) Appl. No.: 12/872,663

(22) Filed: Aug. 31, 2010

(65) Prior Publication Data
US 2010/0324692 A1    Dec. 23, 2010

Related U.S. Application Data

(63) Continuation-in-part of application No. 12/483,807, filed on Jun. 12, 2009, which is a continuation-in-part of application No. 12/371,096, filed on Feb. 13, 2009, which is a continuation-in-part of application No. 12/103,824, filed on Apr. 16, 2008, and a (Continued)

(51) Int. Cl.
*G06Q 10/00* (2012.01)
*A61F 2/38* (2006.01)
(52) U.S. Cl. .................. 705/2; 623/20.35; 623/901
(58) Field of Classification Search .............. 700/117; 705/2
See application file for complete search history.

(56) References Cited

U.S. PATENT DOCUMENTS

| | | | |
|---|---|---|---|
| 1,480,285 A | 1/1924 | Moore |
| 2,181,746 A | 11/1939 | Siebrandt |
| 2,407,845 A | 9/1946 | Nemeyer |
| 2,618,913 A | 11/1952 | Plancon et al. |
| 2,910,978 A | 11/1959 | Urist |
| 3,840,904 A | 10/1974 | Tronzo |
| 4,246,895 A | 1/1981 | Rehder |
| 4,306,866 A | 12/1981 | Weissman |
| 4,324,006 A | 4/1982 | Charnley |
| 4,421,112 A | 12/1983 | Mains et al. |
| 4,436,684 A | 3/1984 | White |
| 4,475,549 A | 10/1984 | Oh |

(Continued)

FOREIGN PATENT DOCUMENTS

| | | |
|---|---|---|
| CA | 2447694 A1 | 12/2002 |
| CA | 2501041 A1 | 4/2004 |

(Continued)

OTHER PUBLICATIONS

International Preliminary Report on Patentability for PCT/US2010/050701 mailed Apr. 12, 2012 claiming benefit of U.S. Appl. No. 12/571,969, filed Oct. 1, 2009.

(Continued)

*Primary Examiner* — Hiep V Nguyen
(74) *Attorney, Agent, or Firm* — Harness, Dickey

(57) ABSTRACT

An orthopedic device includes a femoral implant having a non-custom internal bone engagement surface. The femoral implant includes at least nine parameters adjusted preoperatively to correspond to a specific patient. The parameters can include patient-specific lengths, such as, for example, medial and lateral condyle widths and notch height, and patient-specific medial and lateral angles.

11 Claims, 17 Drawing Sheets

Related U.S. Application Data continuation-in-part of application No. 12/103,834, filed on Apr. 16, 2008, now Pat. No. 7,967,868.

(60) Provisional application No. 61/310,752, filed on Mar. 5, 2010, provisional application No. 60/912,178, filed on Apr. 17, 2007.

U.S. PATENT DOCUMENTS

| Patent No. | | Date | Inventor(s) |
|---|---|---|---|
| 4,506,393 | A | 3/1985 | Murphy |
| 4,524,766 | A | 6/1985 | Petersen |
| 4,619,658 | A | 10/1986 | Pappas et al. |
| 4,621,630 | A | 11/1986 | Kenna |
| 4,632,111 | A | 12/1986 | Roche |
| 4,633,862 | A | 1/1987 | Petersen |
| 4,663,720 | A | 5/1987 | Duret et al. |
| 4,695,283 | A | 9/1987 | Aldinger |
| 4,696,292 | A | 9/1987 | Heiple |
| 4,703,751 | A | 11/1987 | Pohl |
| 4,704,686 | A | 11/1987 | Aldinger |
| 4,721,104 | A | 1/1988 | Kaufman et al. |
| 4,722,330 | A | 2/1988 | Russell et al. |
| 4,778,474 | A | 10/1988 | Homsy |
| 4,800,874 | A | 1/1989 | David et al. |
| 4,821,213 | A | 4/1989 | Cline et al. |
| 4,822,365 | A | 4/1989 | Walker et al. |
| 4,841,975 | A | 6/1989 | Woolson |
| 4,846,161 | A | 7/1989 | Roger |
| 4,871,975 | A | 10/1989 | Nawata et al. |
| 4,893,619 | A | 1/1990 | Dale et al. |
| 4,896,663 | A | 1/1990 | Vandewalls |
| 4,927,422 | A | 5/1990 | Engelhardt |
| 4,936,862 | A | 6/1990 | Walker et al. |
| 4,952,213 | A | 8/1990 | Bowman et al. |
| 4,959,066 | A | 9/1990 | Dunn et al. |
| 4,976,737 | A | 12/1990 | Leake |
| 4,979,949 | A | 12/1990 | Matsen, III et al. |
| 4,985,037 | A | 1/1991 | Petersen |
| 5,002,579 | A | 3/1991 | Copf et al. |
| 5,007,936 | A | 4/1991 | Woolson |
| 5,030,221 | A | 7/1991 | Buechel et al. |
| 5,041,117 | A | 8/1991 | Engelhardt |
| 5,053,037 | A | 10/1991 | Lackey |
| 5,053,039 | A | 10/1991 | Hofmann et al. |
| 5,086,401 | A | 2/1992 | Glassman et al. |
| 5,098,383 | A | 3/1992 | Hemmy et al. |
| 5,098,436 | A | 3/1992 | Ferrante et al. |
| 5,108,425 | A | 4/1992 | Hwang |
| 5,122,144 | A | 6/1992 | Bert et al. |
| 5,129,908 | A | 7/1992 | Petersen |
| 5,129,909 | A | 7/1992 | Sutherland |
| 5,133,760 | A | 7/1992 | Petersen et al. |
| 5,140,777 | A | 8/1992 | Ushiyama et al. |
| 5,150,304 | A | 9/1992 | Berchem et al. |
| 5,176,684 | A | 1/1993 | Ferrante et al. |
| 5,246,444 | A | 9/1993 | Schreiber |
| 5,258,032 | A | 11/1993 | Bertin |
| 5,261,915 | A | 11/1993 | Durlacher et al. |
| 5,274,565 | A | 12/1993 | Reuben |
| 5,299,288 | A | 3/1994 | Glassman et al. |
| 5,300,077 | A | 4/1994 | Howell |
| 5,320,625 | A | 6/1994 | Bertin |
| 5,342,366 | A | 8/1994 | Whiteside et al. |
| 5,344,423 | A | 9/1994 | Dietz et al. |
| 5,360,446 | A | 11/1994 | Kennedy |
| 5,364,402 | A | 11/1994 | Mumme et al. |
| 5,368,858 | A | 11/1994 | Hunziker |
| 5,370,692 | A | 12/1994 | Fink et al. |
| 5,370,699 | A | 12/1994 | Hood et al. |
| 5,405,395 | A | 4/1995 | Coates |
| 5,408,409 | A | 4/1995 | Glassman et al. |
| 5,415,662 | A | 5/1995 | Ferrante et al. |
| 5,417,694 | A | 5/1995 | Marik et al. |
| 5,438,263 | A | 8/1995 | Dworkin et al. |
| 5,440,496 | A | 8/1995 | Andersson et al. |
| 5,448,489 | A | 9/1995 | Reuben |
| 5,449,360 | A | 9/1995 | Schreiber |
| 5,452,407 | A | 9/1995 | Crook |
| 5,454,816 | A | 10/1995 | Ashby |
| 5,472,415 | A | 12/1995 | King et al. |
| 5,474,559 | A | 12/1995 | Bertin et al. |
| 5,490,854 | A | 2/1996 | Fisher et al. |
| 5,496,324 | A | 3/1996 | Barnes |
| 5,507,833 | A | 4/1996 | Bohn |
| 5,514,519 | A | 5/1996 | Neckers |
| 5,520,695 | A | 5/1996 | Luckman |
| 5,527,317 | A | 6/1996 | Ashby et al. |
| 5,539,649 | A | 7/1996 | Walsh et al. |
| 5,540,695 | A | 7/1996 | Levy |
| 5,549,688 | A * | 8/1996 | Ries et al. ........... 623/20.35 |
| 5,554,190 | A | 9/1996 | Draenert |
| 5,560,096 | A | 10/1996 | Stephens |
| 5,571,110 | A | 11/1996 | Matsen, III et al. |
| 5,578,037 | A | 11/1996 | Sanders et al. |
| 5,595,703 | A | 1/1997 | Swaelens et al. |
| 5,607,431 | A | 3/1997 | Dudasik et al. |
| 5,613,969 | A | 3/1997 | Jenkins, Jr. |
| 5,620,448 | A | 4/1997 | Puddu |
| 5,634,927 | A | 6/1997 | Houston et al. |
| 5,658,294 | A | 8/1997 | Sederholm |
| 5,662,656 | A | 9/1997 | White |
| 5,671,018 | A | 9/1997 | Ohara et al. |
| 5,677,107 | A | 10/1997 | Neckers |
| 5,681,354 | A | 10/1997 | Eckhoff |
| 5,682,886 | A | 11/1997 | Delp et al. |
| 5,690,635 | A | 11/1997 | Matsen, III et al. |
| 5,702,460 | A | 12/1997 | Carls et al. |
| 5,704,941 | A | 1/1998 | Jacober et al. |
| 5,722,978 | A | 3/1998 | Jenkins, Jr. |
| 5,725,376 | A | 3/1998 | Poirier |
| 5,725,593 | A | 3/1998 | Caracciolo |
| 5,735,277 | A | 4/1998 | Schuster |
| 5,748,767 | A | 5/1998 | Raab |
| 5,749,875 | A | 5/1998 | Puddu |
| 5,749,876 | A | 5/1998 | Duvillier et al. |
| 5,762,125 | A | 6/1998 | Mastrorio |
| 5,768,134 | A | 6/1998 | Swaelens et al. |
| 5,769,092 | A | 6/1998 | Williamson, Jr. |
| 5,786,217 | A | 7/1998 | Tubo et al. |
| 5,792,143 | A | 8/1998 | Samuelson et al. |
| 5,798,924 | A | 8/1998 | Eufinger et al. |
| 5,799,055 | A | 8/1998 | Peshkin et al. |
| 5,860,981 | A | 1/1999 | Bertin et al. |
| 5,871,018 | A | 2/1999 | Delp et al. |
| 5,876,456 | A | 3/1999 | Sederholm et al. |
| 5,879,398 | A | 3/1999 | Swarts et al. |
| 5,879,402 | A | 3/1999 | Lawes et al. |
| 5,880,976 | A | 3/1999 | DiGioia, III et al. |
| 5,885,297 | A | 3/1999 | Matsen, III |
| 5,885,298 | A | 3/1999 | Herrington et al. |
| 5,895,389 | A | 4/1999 | Schenk et al. |
| 5,899,907 | A | 5/1999 | Johnson |
| 5,901,060 | A | 5/1999 | Schall et al. |
| 5,911,724 | A | 6/1999 | Wehrli |
| 5,921,988 | A | 7/1999 | Legrand |
| 5,925,049 | A | 7/1999 | Gustilo et al. |
| 5,942,370 | A | 8/1999 | Neckers |
| 5,967,777 | A | 10/1999 | Klein et al. |
| 5,976,149 | A | 11/1999 | Masini |
| 5,980,526 | A | 11/1999 | Johnson et al. |
| 6,033,415 | A | 3/2000 | Mittelstadt et al. |
| 6,059,789 | A | 5/2000 | Dinger et al. |
| 6,059,833 | A | 5/2000 | Doets |
| 6,086,593 | A | 7/2000 | Bonutti |
| 6,120,510 | A | 9/2000 | Albrektsson et al. |
| 6,120,544 | A | 9/2000 | Grundei et al. |
| 6,126,690 | A | 10/2000 | Ateshian et al. |
| 6,136,033 | A | 10/2000 | Suemer |
| 6,156,069 | A | 12/2000 | Amstutz |
| 6,161,080 | A | 12/2000 | Aouni-Ateshian et al. |
| 6,187,010 | B1 | 2/2001 | Masini |
| 6,195,615 | B1 | 2/2001 | Lysen |
| 6,203,546 | B1 | 3/2001 | MacMahon |
| 6,205,411 | B1 | 3/2001 | DiGioia, III et al. |
| 6,206,927 | B1 | 3/2001 | Fell et al. |
| 6,254,604 | B1 | 7/2001 | Howell |

| | | |
|---|---|---|
| 6,258,097 B1 | 7/2001 | Cook et al. |
| 6,264,698 B1 | 7/2001 | Lawes et al. |
| 6,273,891 B1 | 8/2001 | Masini |
| 6,290,727 B1 | 9/2001 | Otto et al. |
| 6,293,971 B1 | 9/2001 | Nelson et al. |
| 6,312,258 B1 | 11/2001 | Ashman |
| 6,312,473 B1 | 11/2001 | Oshida |
| 6,319,285 B1 | 11/2001 | Chamier et al. |
| 6,325,829 B1 | 12/2001 | Schmotzer |
| 6,343,987 B2 | 2/2002 | Hayama et al. |
| 6,354,011 B1 | 3/2002 | Albrecht |
| 6,379,299 B1 | 4/2002 | Borodulin et al. |
| 6,383,228 B1 | 5/2002 | Schmotzer |
| 6,391,251 B1 | 5/2002 | Keicher et al. |
| 6,395,005 B1 | 5/2002 | Lovell |
| 6,427,698 B1 | 8/2002 | Yoon |
| 6,459,948 B1 | 10/2002 | Ateshian et al. |
| 6,463,351 B1 | 10/2002 | Clynch |
| 6,475,243 B1 | 11/2002 | Sheldon et al. |
| 6,482,236 B2 | 11/2002 | Habecker |
| 6,488,715 B1 | 12/2002 | Pope et al. |
| 6,503,255 B1 | 1/2003 | Albrektsson et al. |
| 6,510,334 B1 | 1/2003 | Schuster et al. |
| 6,514,259 B2 | 2/2003 | Picard et al. |
| 6,517,583 B1 | 2/2003 | Pope et al. |
| 6,520,964 B2 | 2/2003 | Tallarida et al. |
| 6,533,737 B1 | 3/2003 | Brosseau et al. |
| 6,547,823 B2 | 4/2003 | Scarborough et al. |
| 6,554,837 B1 | 4/2003 | Hauri et al. |
| 6,556,008 B2 | 4/2003 | Thesen |
| 6,558,391 B2 | 5/2003 | Axelson, Jr. et al. |
| 6,558,428 B2 | 5/2003 | Park |
| 6,564,085 B2 | 5/2003 | Meaney et al. |
| 6,567,681 B1 | 5/2003 | Lindequist |
| 6,575,980 B1 | 6/2003 | Robie et al. |
| 6,575,982 B1 | 6/2003 | Bonutti |
| 6,591,581 B2 | 7/2003 | Schmieding |
| 6,605,293 B1 | 8/2003 | Giordano et al. |
| 6,622,567 B1 | 9/2003 | Hamel et al. |
| 6,629,999 B1 | 10/2003 | Serafin, Jr. |
| 6,641,617 B1 | 11/2003 | Merrill et al. |
| 6,682,566 B2 | 1/2004 | Draenert |
| 6,696,073 B2 | 2/2004 | Boyce et al. |
| 6,697,664 B2 | 2/2004 | Kienzle, III et al. |
| 6,701,174 B1 | 3/2004 | Krause et al. |
| 6,709,462 B2 | 3/2004 | Hanssen |
| 6,711,431 B2 | 3/2004 | Sarin et al. |
| 6,711,432 B1 | 3/2004 | Krause et al. |
| 6,712,856 B1 | 3/2004 | Carignan et al. |
| 6,716,249 B2 | 4/2004 | Hyde |
| 6,725,077 B1 | 4/2004 | Balloni et al. |
| 6,738,657 B1 | 5/2004 | Franklin et al. |
| 6,740,092 B2 | 5/2004 | Lombardo et al. |
| 6,749,638 B1 | 6/2004 | Saladino |
| 6,750,653 B1 | 6/2004 | Zou et al. |
| 6,772,026 B2 | 8/2004 | Bradbury et al. |
| 6,780,190 B2 | 8/2004 | Maroney |
| 6,786,930 B2 | 9/2004 | Biscup |
| 6,799,066 B2 | 9/2004 | Steines et al. |
| 6,823,871 B2 | 11/2004 | Schmieding |
| 6,827,723 B2 | 12/2004 | Carson |
| 6,887,247 B1 | 5/2005 | Couture et al. |
| 6,905,514 B2 | 6/2005 | Carignan et al. |
| 6,923,817 B2 | 8/2005 | Carson et al. |
| 6,923,831 B2 | 8/2005 | Fell et al. |
| 6,932,842 B1 | 8/2005 | Litschko et al. |
| 6,942,475 B2 | 9/2005 | Ensign et al. |
| 6,944,518 B2 | 9/2005 | Roose |
| 6,945,976 B2 | 9/2005 | Ball et al. |
| 6,953,480 B2 | 10/2005 | Mears et al. |
| 6,960,216 B2 | 11/2005 | Kolb et al. |
| 6,990,220 B2 | 1/2006 | Ellis et al. |
| 7,029,479 B2 | 4/2006 | Tallarida et al. |
| 7,042,222 B2 | 5/2006 | Zheng et al. |
| 7,048,741 B2 | 5/2006 | Swanson |
| 7,050,877 B2 | 5/2006 | Iseki et al. |
| 7,060,074 B2 | 6/2006 | Rosa et al. |
| 7,074,241 B2 | 7/2006 | McKinnon |
| RE39,301 E | 9/2006 | Bertin |
| 7,104,997 B2 | 9/2006 | Lionberger et al. |
| 7,105,026 B2 | 9/2006 | Johnson et al. |
| 7,115,131 B2 | 10/2006 | Engh et al. |
| 7,141,053 B2 | 11/2006 | Rosa et al. |
| 7,169,185 B2 | 1/2007 | Sidebotham |
| 7,176,466 B2 | 2/2007 | Rousso et al. |
| 7,184,814 B2 | 2/2007 | Lang et al. |
| 7,198,628 B2 | 4/2007 | Ondrla et al. |
| 7,218,232 B2 | 5/2007 | DiSilvestro et al. |
| 7,239,908 B1 | 7/2007 | Alexander et al. |
| 7,241,315 B2 | 7/2007 | Evans |
| 7,255,702 B2 | 8/2007 | Serra et al. |
| 7,258,701 B2 | 8/2007 | Aram et al. |
| 7,275,218 B2 | 9/2007 | Petrella et al. |
| 7,282,054 B2 | 10/2007 | Steffensmeier et al. |
| 7,294,133 B2 | 11/2007 | Zink et al. |
| 7,297,164 B2 | 11/2007 | Johnson et al. |
| 7,309,339 B2 | 12/2007 | Cusick et al. |
| 7,333,013 B2 | 2/2008 | Berger |
| 7,335,231 B2 | 2/2008 | McLean |
| 7,371,260 B2 | 5/2008 | Malinin |
| 7,383,164 B2 | 6/2008 | Aram et al. |
| 7,385,498 B2 | 6/2008 | Dobosz |
| 7,388,972 B2 | 6/2008 | Kitson |
| 7,392,076 B2 | 6/2008 | Moctezuma de La Barrera |
| 7,427,200 B2 * | 9/2008 | Noble et al. ............... 434/274 |
| 7,427,272 B2 | 9/2008 | Richard et al. |
| 7,468,075 B2 | 12/2008 | Lang et al. |
| 7,474,223 B2 | 1/2009 | Nycz et al. |
| 7,488,325 B2 | 2/2009 | Qian |
| 7,494,510 B2 | 2/2009 | Zweymuller |
| 7,517,365 B2 | 4/2009 | Carignan et al. |
| 7,527,631 B2 | 5/2009 | Maroney et al. |
| 7,534,263 B2 | 5/2009 | Burdulis, Jr. et al. |
| 7,542,791 B2 | 6/2009 | Mire et al. |
| 7,559,931 B2 | 7/2009 | Stone |
| 7,575,602 B2 | 8/2009 | Amirouche et al. |
| 7,578,851 B2 | 8/2009 | Dong et al. |
| 7,582,091 B2 | 9/2009 | Duncan et al. |
| 7,591,821 B2 | 9/2009 | Kelman |
| 7,601,155 B2 | 10/2009 | Petersen |
| 7,604,639 B2 | 10/2009 | Swanson |
| 7,611,516 B2 | 11/2009 | Maroney |
| 7,618,451 B2 | 11/2009 | Berez et al. |
| 7,621,915 B2 | 11/2009 | Frederick et al. |
| 7,625,409 B2 | 12/2009 | Saltzman et al. |
| 7,646,161 B2 | 1/2010 | Albu-Schaffer et al. |
| 7,651,501 B2 | 1/2010 | Penenberg et al. |
| 7,670,345 B2 | 3/2010 | Plassky et al. |
| 7,682,398 B2 | 3/2010 | Croxton et al. |
| 7,695,477 B2 | 4/2010 | Creger et al. |
| 7,695,521 B2 | 4/2010 | Ely et al. |
| 7,699,847 B2 | 4/2010 | Sheldon et al. |
| 7,704,253 B2 | 4/2010 | Bastian et al. |
| 7,723,395 B2 | 5/2010 | Ringeisen et al. |
| 7,780,672 B2 | 8/2010 | Metzger et al. |
| 7,780,740 B2 | 8/2010 | Steinberg |
| 7,794,466 B2 | 9/2010 | Merchant et al. |
| 7,794,467 B2 | 9/2010 | McGinley et al. |
| 7,794,504 B2 | 9/2010 | Case |
| 7,806,896 B1 | 10/2010 | Bonutti |
| 7,809,184 B2 | 10/2010 | Neubauer et al. |
| 7,819,925 B2 | 10/2010 | King et al. |
| 7,828,806 B2 | 11/2010 | Graf et al. |
| 7,879,109 B2 | 2/2011 | Borden et al. |
| 7,892,261 B2 | 2/2011 | Bonutti |
| 7,896,921 B2 | 3/2011 | Smith et al. |
| 7,935,119 B2 | 5/2011 | Ammann et al. |
| 7,935,150 B2 | 5/2011 | Carignan et al. |
| 7,938,861 B2 | 5/2011 | King et al. |
| 7,959,637 B2 | 6/2011 | Fox et al. |
| 7,962,196 B2 | 6/2011 | Tuma |
| 7,963,968 B2 | 6/2011 | Dees, Jr. |
| 7,967,823 B2 | 6/2011 | Ammann et al. |
| 7,967,868 B2 | 6/2011 | White et al. |
| 7,974,677 B2 | 7/2011 | Mire et al. |
| 7,981,158 B2 | 7/2011 | Fitz et al. |
| 7,993,353 B2 | 8/2011 | Rossner et al. |
| 8,062,301 B2 | 11/2011 | Ammann et al. |

| | | |
|---|---|---|
| 8,070,752 B2 | 12/2011 | Metzger et al. |
| 8,083,745 B2 | 12/2011 | Lang et al. |
| 8,083,746 B2 | 12/2011 | Novak |
| 8,083,749 B2 | 12/2011 | Taber |
| 8,086,336 B2 | 12/2011 | Christensen |
| 8,092,465 B2 | 1/2012 | Metzger et al. |
| 8,133,230 B2 | 3/2012 | Stevens et al. |
| 8,137,406 B2 | 3/2012 | Novak et al. |
| 8,182,489 B2 | 5/2012 | Horacek |
| 8,192,441 B2 | 6/2012 | Collazo |
| 8,241,292 B2 | 8/2012 | Collazo |
| 8,303,596 B2 | 11/2012 | Plaßky et al. |
| 2001/0005797 A1 | 6/2001 | Barlow et al. |
| 2001/0011190 A1 | 8/2001 | Park |
| 2001/0054478 A1 | 12/2001 | Watanabe et al. |
| 2002/0007294 A1 | 1/2002 | Bradbury et al. |
| 2002/0052606 A1 | 5/2002 | Bonutti |
| 2002/0059049 A1 | 5/2002 | Bradbury et al. |
| 2002/0082741 A1 | 6/2002 | Mazumder et al. |
| 2002/0087274 A1 | 7/2002 | Alexander et al. |
| 2002/0107522 A1 | 8/2002 | Picard et al. |
| 2002/0128872 A1 | 9/2002 | Giammattei |
| 2002/0147415 A1 | 10/2002 | Martelli |
| 2003/0009171 A1 | 1/2003 | Tornier |
| 2003/0009234 A1 | 1/2003 | Treacy et al. |
| 2003/0011624 A1 | 1/2003 | Ellis |
| 2003/0018338 A1 | 1/2003 | Axelson et al. |
| 2003/0039676 A1 | 2/2003 | Boyce et al. |
| 2003/0055502 A1 | 3/2003 | Lang et al. |
| 2003/0105526 A1 | 6/2003 | Bryant et al. |
| 2003/0109784 A1 | 6/2003 | Loh et al. |
| 2003/0120276 A1 | 6/2003 | Tallarida et al. |
| 2003/0139817 A1 | 7/2003 | Tuke et al. |
| 2003/0158606 A1 | 8/2003 | Coon et al. |
| 2003/0171757 A1 | 9/2003 | Coon et al. |
| 2003/0216669 A1 | 11/2003 | Lang et al. |
| 2004/0018144 A1 | 1/2004 | Briscoe |
| 2004/0030245 A1 | 2/2004 | Noble et al. |
| 2004/0054372 A1 | 3/2004 | Corden et al. |
| 2004/0068187 A1 | 4/2004 | Krause et al. |
| 2004/0092932 A1 | 5/2004 | Aubin et al. |
| 2004/0098133 A1 | 5/2004 | Carignan et al. |
| 2004/0102852 A1 | 5/2004 | Johnson et al. |
| 2004/0102866 A1 | 5/2004 | Harris et al. |
| 2004/0106926 A1 | 6/2004 | Leitner et al. |
| 2004/0115586 A1 | 6/2004 | Andreiko et al. |
| 2004/0122439 A1 | 6/2004 | Dwyer et al. |
| 2004/0128026 A1 | 7/2004 | Harris et al. |
| 2004/0133276 A1 | 7/2004 | Lang et al. |
| 2004/0138754 A1 | 7/2004 | Lang et al. |
| 2004/0143336 A1 | 7/2004 | Burkinshaw |
| 2004/0147927 A1 | 7/2004 | Tsougarakis et al. |
| 2004/0148026 A1 | 7/2004 | Bonutti |
| 2004/0153079 A1 | 8/2004 | Tsougarakis et al. |
| 2004/0153087 A1 | 8/2004 | Sanford et al. |
| 2004/0158254 A1 | 8/2004 | Eisermann |
| 2004/0162619 A1 | 8/2004 | Blaylock et al. |
| 2004/0167390 A1 | 8/2004 | Alexander et al. |
| 2004/0171924 A1 | 9/2004 | Mire et al. |
| 2004/0172137 A1 | 9/2004 | Blaylock et al. |
| 2004/0181144 A1 | 9/2004 | Cinquin et al. |
| 2004/0204644 A1 | 10/2004 | Tsougarakis et al. |
| 2004/0204760 A1 | 10/2004 | Fitz et al. |
| 2004/0212586 A1 | 10/2004 | Denny |
| 2004/0220583 A1 | 11/2004 | Pieczynski et al. |
| 2004/0236341 A1 | 11/2004 | Petersen |
| 2004/0236424 A1 | 11/2004 | Berez et al. |
| 2004/0243481 A1 | 12/2004 | Bradbury et al. |
| 2004/0254584 A1 | 12/2004 | Sarin et al. |
| 2004/0260301 A1 | 12/2004 | Lionberger et al. |
| 2005/0008887 A1 | 1/2005 | Haymann et al. |
| 2005/0010227 A1 | 1/2005 | Paul |
| 2005/0010300 A1 | 1/2005 | Disilvestro et al. |
| 2005/0015022 A1 | 1/2005 | Richard et al. |
| 2005/0019664 A1 | 1/2005 | Matsumoto |
| 2005/0027303 A1 | 2/2005 | Lionberger et al. |
| 2005/0027361 A1 | 2/2005 | Reiley |
| 2005/0043806 A1 | 2/2005 | Cook et al. |
| 2005/0043837 A1 | 2/2005 | Rubbert et al. |
| 2005/0049524 A1 | 3/2005 | Lefevre et al. |
| 2005/0049603 A1 | 3/2005 | Calton et al. |
| 2005/0059873 A1 | 3/2005 | Glozman et al. |
| 2005/0060040 A1 | 3/2005 | Auxepaules et al. |
| 2005/0065628 A1 | 3/2005 | Roose |
| 2005/0070897 A1 | 3/2005 | Petersen |
| 2005/0071015 A1 | 3/2005 | Sekel |
| 2005/0075641 A1 | 4/2005 | Singhatat et al. |
| 2005/0096535 A1 | 5/2005 | de la Barrera |
| 2005/0113841 A1 | 5/2005 | Sheldon et al. |
| 2005/0113846 A1 | 5/2005 | Carson |
| 2005/0119664 A1 | 6/2005 | Carignan et al. |
| 2005/0131662 A1 | 6/2005 | Ascenzi et al. |
| 2005/0137708 A1 | 6/2005 | Clark |
| 2005/0148843 A1 | 7/2005 | Roose |
| 2005/0149042 A1 | 7/2005 | Metzger |
| 2005/0171545 A1 | 8/2005 | Walsh et al. |
| 2005/0177245 A1 | 8/2005 | Leatherbury et al. |
| 2005/0203536 A1 | 9/2005 | Laffargue et al. |
| 2005/0203540 A1 | 9/2005 | Broyles |
| 2005/0216305 A1 | 9/2005 | Funderud |
| 2005/0222573 A1 | 10/2005 | Branch et al. |
| 2005/0228393 A1 | 10/2005 | Williams et al. |
| 2005/0234461 A1 | 10/2005 | Burdulis et al. |
| 2005/0234468 A1 | 10/2005 | Carson |
| 2005/0240195 A1 | 10/2005 | Axelson et al. |
| 2005/0240267 A1 | 10/2005 | Randall et al. |
| 2005/0244239 A1 | 11/2005 | Shimp |
| 2005/0245934 A1 | 11/2005 | Tuke et al. |
| 2005/0245936 A1 | 11/2005 | Tuke et al. |
| 2005/0251147 A1 | 11/2005 | Novak |
| 2005/0267353 A1 | 12/2005 | Marquart et al. |
| 2005/0267485 A1 | 12/2005 | Cordes et al. |
| 2005/0267584 A1 | 12/2005 | Burdulis et al. |
| 2005/0273114 A1 | 12/2005 | Novak |
| 2005/0283252 A1 | 12/2005 | Coon et al. |
| 2005/0283253 A1 | 12/2005 | Coon et al. |
| 2006/0004284 A1 | 1/2006 | Grunschlager et al. |
| 2006/0015120 A1 | 1/2006 | Richard et al. |
| 2006/0030853 A1 | 2/2006 | Haines |
| 2006/0038520 A1 | 2/2006 | Negoro et al. |
| 2006/0052725 A1 | 3/2006 | Santilli |
| 2006/0058803 A1 | 3/2006 | Cuckler et al. |
| 2006/0058884 A1 | 3/2006 | Aram et al. |
| 2006/0058886 A1 | 3/2006 | Wozencroft |
| 2006/0089621 A1 | 4/2006 | Fard |
| 2006/0093988 A1 | 5/2006 | Swaelens et al. |
| 2006/0094951 A1 | 5/2006 | Dean et al. |
| 2006/0095044 A1 | 5/2006 | Grady et al. |
| 2006/0100832 A1 | 5/2006 | Bowman |
| 2006/0111722 A1 | 5/2006 | Bouadi |
| 2006/0122616 A1 | 6/2006 | Bennett et al. |
| 2006/0136058 A1 | 6/2006 | Pietrzak |
| 2006/0142657 A1 | 6/2006 | Quaid et al. |
| 2006/0155380 A1 | 7/2006 | Clemow et al. |
| 2006/0161167 A1 | 7/2006 | Myers et al. |
| 2006/0172263 A1 | 8/2006 | Quadling et al. |
| 2006/0178497 A1 | 8/2006 | Gevaert et al. |
| 2006/0184177 A1 | 8/2006 | Echeverri |
| 2006/0190086 A1 | 8/2006 | Clemow et al. |
| 2006/0195111 A1 | 8/2006 | Couture |
| 2006/0195194 A1 | 8/2006 | Gunther |
| 2006/0195198 A1 | 8/2006 | James |
| 2006/0200158 A1 | 9/2006 | Farling et al. |
| 2006/0204932 A1 | 9/2006 | Haymann et al. |
| 2006/0210644 A1 | 9/2006 | Levin |
| 2006/0217808 A1 | 9/2006 | Novak et al. |
| 2006/0235421 A1 | 10/2006 | Rosa et al. |
| 2006/0241635 A1 | 10/2006 | Stumpo et al. |
| 2006/0241636 A1 | 10/2006 | Novak et al. |
| 2006/0271058 A1 | 11/2006 | Ashton et al. |
| 2006/0276796 A1 | 12/2006 | Creger et al. |
| 2006/0276797 A1 | 12/2006 | Botimer |
| 2006/0287733 A1 | 12/2006 | Bonutti |
| 2006/0293681 A1 | 12/2006 | Claypool et al. |
| 2007/0015995 A1 | 1/2007 | Lang et al. |
| 2007/0016209 A1 | 1/2007 | Ammann et al. |
| 2007/0027680 A1 | 2/2007 | Ashley et al. |
| 2007/0066917 A1 | 3/2007 | Hodorek et al. |

| | | | | | | |
|---|---|---|---|---|---|---|
| 2007/0073137 A1 | 3/2007 | Schoenefeld | | 2008/0208200 A1 | 8/2008 | Crofford |
| 2007/0083214 A1 | 4/2007 | Duncan et al. | | 2008/0208353 A1 | 8/2008 | Kumar et al. |
| 2007/0083266 A1 | 4/2007 | Lang | | 2008/0215059 A1 | 9/2008 | Carignan et al. |
| 2007/0100258 A1 | 5/2007 | Shoham et al. | | 2008/0230422 A1 | 9/2008 | Pleil et al. |
| 2007/0100450 A1 | 5/2007 | Hodorek | | 2008/0234664 A1 | 9/2008 | May et al. |
| 2007/0100462 A1 | 5/2007 | Lang et al. | | 2008/0234683 A1 | 9/2008 | May |
| 2007/0118055 A1 | 5/2007 | McCombs | | 2008/0234685 A1 | 9/2008 | Gjerde |
| 2007/0118138 A1 | 5/2007 | Seo et al. | | 2008/0234833 A1 | 9/2008 | Bandoh et al. |
| 2007/0118243 A1 | 5/2007 | Schroeder et al. | | 2008/0243127 A1 | 10/2008 | Lang et al. |
| 2007/0150068 A1 | 6/2007 | Dong et al. | | 2008/0255674 A1 | 10/2008 | Rahaman et al. |
| 2007/0156066 A1 | 7/2007 | McGinley et al. | | 2008/0257363 A1 | 10/2008 | Schoenefeld et al. |
| 2007/0156171 A1 | 7/2007 | Lang et al. | | 2008/0262500 A1 | 10/2008 | Collazo |
| 2007/0162038 A1 | 7/2007 | Tuke | | 2008/0262624 A1 | 10/2008 | White et al. |
| 2007/0162039 A1 | 7/2007 | Wozencroft | | 2008/0269906 A1 | 10/2008 | Iannotti et al. |
| 2007/0173946 A1 | 7/2007 | Bonutti | | 2008/0275452 A1 | 11/2008 | Lang et al. |
| 2007/0173948 A1 | 7/2007 | Meridew et al. | | 2008/0281328 A1 | 11/2008 | Lang et al. |
| 2007/0185498 A2 | 8/2007 | Lavallee | | 2008/0281329 A1 | 11/2008 | Fitz et al. |
| 2007/0191962 A1 | 8/2007 | Jones et al. | | 2008/0281426 A1 | 11/2008 | Fitz et al. |
| 2007/0198022 A1 | 8/2007 | Lang et al. | | 2008/0287954 A1 | 11/2008 | Kunz et al. |
| 2007/0203430 A1 | 8/2007 | Lang et al. | | 2008/0294170 A1 | 11/2008 | O'Brien |
| 2007/0203605 A1 | 8/2007 | Melton et al. | | 2008/0294266 A1 | 11/2008 | Steinberg |
| 2007/0219639 A1 | 9/2007 | Otto et al. | | 2008/0300600 A1 | 12/2008 | Guelat et al. |
| 2007/0219640 A1 | 9/2007 | Steinberg | | 2008/0306485 A1 | 12/2008 | Coon et al. |
| 2007/0224238 A1 | 9/2007 | Mansmann et al. | | 2008/0306558 A1 | 12/2008 | Hakki |
| 2007/0226986 A1 | 10/2007 | Park et al. | | 2008/0312659 A1 | 12/2008 | Metzger et al. |
| 2007/0233121 A1 | 10/2007 | Carson et al. | | 2008/0319448 A1 | 12/2008 | Lavallee et al. |
| 2007/0233136 A1 | 10/2007 | Wozencroft | | 2009/0012526 A1 | 1/2009 | Fletcher |
| 2007/0233140 A1 | 10/2007 | Metzger et al. | | 2009/0018546 A1 | 1/2009 | Daley |
| 2007/0233141 A1 | 10/2007 | Park et al. | | 2009/0018666 A1 | 1/2009 | Grundei et al. |
| 2007/0233269 A1 | 10/2007 | Steines et al. | | 2009/0024131 A1 | 1/2009 | Metzger et al. |
| 2007/0233272 A1 | 10/2007 | Boyce et al. | | 2009/0043556 A1 | 2/2009 | Axelson et al. |
| 2007/0238069 A1 | 10/2007 | Lovald et al. | | 2009/0076371 A1 | 3/2009 | Lang et al. |
| 2007/0239282 A1 | 10/2007 | Caylor et al. | | 2009/0076512 A1 | 3/2009 | Ammann et al. |
| 2007/0239481 A1 | 10/2007 | DiSilvestro et al. | | 2009/0076520 A1 | 3/2009 | Choi |
| 2007/0250169 A1 | 10/2007 | Lang | | 2009/0082770 A1 | 3/2009 | Worner et al. |
| 2007/0253617 A1 | 11/2007 | Arata et al. | | 2009/0082774 A1 | 3/2009 | Oti et al. |
| 2007/0255288 A1 | 11/2007 | Mahfouz et al. | | 2009/0087276 A1 | 4/2009 | Rose |
| 2007/0255412 A1 | 11/2007 | Hajaj et al. | | 2009/0088674 A1 | 4/2009 | Caillouette et al. |
| 2007/0262867 A1 | 11/2007 | Westrick et al. | | 2009/0088753 A1 | 4/2009 | Aram et al. |
| 2007/0272747 A1 | 11/2007 | Woods et al. | | 2009/0088754 A1 | 4/2009 | Aker et al. |
| 2007/0276224 A1 | 11/2007 | Lang et al. | | 2009/0088755 A1 | 4/2009 | Aker et al. |
| 2007/0276400 A1 | 11/2007 | Moore et al. | | 2009/0088758 A1 | 4/2009 | Bennett |
| 2007/0276501 A1 | 11/2007 | Betz et al. | | 2009/0088759 A1 | 4/2009 | Aram et al. |
| 2007/0288029 A1 | 12/2007 | Justin et al. | | 2009/0088760 A1 | 4/2009 | Aram et al. |
| 2007/0288030 A1 | 12/2007 | Metzger et al. | | 2009/0088761 A1 | 4/2009 | Roose et al. |
| 2008/0009952 A1 | 1/2008 | Hodge | | 2009/0088763 A1 | 4/2009 | Aram et al. |
| 2008/0015599 A1 | 1/2008 | D'Alessio et al. | | 2009/0088865 A1 | 4/2009 | Brehm |
| 2008/0015603 A1 | 1/2008 | Collazo | | 2009/0088866 A1 | 4/2009 | Case |
| 2008/0015604 A1 | 1/2008 | Collazo | | 2009/0089034 A1 | 4/2009 | Penney et al. |
| 2008/0015605 A1 | 1/2008 | Collazo | | 2009/0089081 A1 | 4/2009 | Haddad |
| 2008/0021299 A1 | 1/2008 | Meulink | | 2009/0093815 A1 | 4/2009 | Fletcher et al. |
| 2008/0021494 A1 | 1/2008 | Schmelzeisen-Redeker et al. | | 2009/0093816 A1 | 4/2009 | Roose et al. |
| 2008/0021567 A1 | 1/2008 | Meulink et al. | | 2009/0096613 A1 | 4/2009 | Westrick |
| 2008/0027563 A1 | 1/2008 | Johnson et al. | | 2009/0099567 A1 | 4/2009 | Zajac |
| 2008/0033442 A1 | 2/2008 | Amiot et al. | | 2009/0105837 A1 | 4/2009 | Lafosse et al. |
| 2008/0039850 A1 | 2/2008 | Rowley et al. | | 2009/0118736 A1 | 5/2009 | Kreuzer |
| 2008/0051799 A1 | 2/2008 | Bonutti | | 2009/0118769 A1 | 5/2009 | Sixto, Jr. et al. |
| 2008/0051910 A1 | 2/2008 | Kammerzell et al. | | 2009/0131941 A1 | 5/2009 | Park et al. |
| 2008/0058945 A1 | 3/2008 | Hajaj et al. | | 2009/0131942 A1 | 5/2009 | Aker et al. |
| 2008/0058947 A1 | 3/2008 | Earl et al. | | 2009/0138020 A1 | 5/2009 | Park et al. |
| 2008/0062183 A1 | 3/2008 | Swaelens | | 2009/0149965 A1 | 6/2009 | Quaid |
| 2008/0065225 A1 | 3/2008 | Wasielewski et al. | | 2009/0149977 A1 | 6/2009 | Schendel |
| 2008/0097451 A1 | 4/2008 | Chen et al. | | 2009/0151736 A1 | 6/2009 | Belcher et al. |
| 2008/0112996 A1 | 5/2008 | Harlow et al. | | 2009/0157083 A1 | 6/2009 | Park et al. |
| 2008/0114370 A1 | 5/2008 | Schoenefeld | | 2009/0163922 A1 | 6/2009 | Meridew et al. |
| 2008/0133022 A1 | 6/2008 | Caylor | | 2009/0163923 A1 | 6/2009 | Flett et al. |
| 2008/0140081 A1 | 6/2008 | Heavener et al. | | 2009/0164024 A1 | 6/2009 | Rudan et al. |
| 2008/0140209 A1 | 6/2008 | Iannotti et al. | | 2009/0177282 A1 | 7/2009 | Bureau et al. |
| 2008/0140213 A1 | 6/2008 | Ammann et al. | | 2009/0187193 A1 | 7/2009 | Maroney et al. |
| 2008/0146969 A1 | 6/2008 | Kurtz | | 2009/0209884 A1 | 8/2009 | Van Vorhis et al. |
| 2008/0147072 A1 | 6/2008 | Park et al. | | 2009/0209961 A1 | 8/2009 | Ferrante et al. |
| 2008/0147073 A1 | 6/2008 | Ammann et al. | | 2009/0222014 A1 | 9/2009 | Bojarski et al. |
| 2008/0161815 A1 | 7/2008 | Schoenefeld et al. | | 2009/0222015 A1 | 9/2009 | Park et al. |
| 2008/0172125 A1 | 7/2008 | Ek | | 2009/0222016 A1 | 9/2009 | Park et al. |
| 2008/0195099 A1 | 8/2008 | Minas | | 2009/0222103 A1 | 9/2009 | Fitz et al. |
| 2008/0195107 A1 | 8/2008 | Cuckler et al. | | 2009/0228016 A1 | 9/2009 | Alvarez et al. |
| 2008/0195108 A1 | 8/2008 | Bhatnagar et al. | | 2009/0234360 A1 | 9/2009 | Alexander |
| 2008/0195216 A1 | 8/2008 | Philipp | | 2009/0248044 A1 | 10/2009 | Amiot et al. |
| 2008/0200926 A1 | 8/2008 | Verard et al. | | 2009/0254093 A1 | 10/2009 | White et al. |

| | | | |
|---|---|---|---|
| 2009/0254367 A1 | 10/2009 | Belcher et al. |
| 2009/0270868 A1 | 10/2009 | Park et al. |
| 2009/0274350 A1 | 11/2009 | Pavlovskaia et al. |
| 2009/0287217 A1 | 11/2009 | Ammann et al. |
| 2009/0306676 A1 | 12/2009 | Lang et al. |
| 2009/0307893 A1 | 12/2009 | Burdulis, Jr. et al. |
| 2009/0318836 A1 | 12/2009 | Stone et al. |
| 2009/0318921 A1 | 12/2009 | White et al. |
| 2010/0010493 A1 | 1/2010 | Dower |
| 2010/0016984 A1 | 1/2010 | Trabish |
| 2010/0016986 A1 | 1/2010 | Trabish |
| 2010/0023015 A1 | 1/2010 | Park |
| 2010/0030231 A1 | 2/2010 | Revie et al. |
| 2010/0042105 A1 | 2/2010 | Park et al. |
| 2010/0049195 A1 | 2/2010 | Park et al. |
| 2010/0057088 A1 | 3/2010 | Shah |
| 2010/0076439 A1 | 3/2010 | Hatch |
| 2010/0076505 A1 | 3/2010 | Borja |
| 2010/0076563 A1 | 3/2010 | Otto et al. |
| 2010/0076571 A1 | 3/2010 | Hatch |
| 2010/0082034 A1 | 4/2010 | Remia |
| 2010/0082035 A1 | 4/2010 | Keefer |
| 2010/0087829 A1 | 4/2010 | Metzger et al. |
| 2010/0094295 A1 | 4/2010 | Schnieders et al. |
| 2010/0105011 A1 | 4/2010 | Karkar et al. |
| 2010/0121334 A1 | 5/2010 | Couture et al. |
| 2010/0121335 A1 | 5/2010 | Penenberg et al. |
| 2010/0137869 A1 | 6/2010 | Borja et al. |
| 2010/0137924 A1 | 6/2010 | Tuke et al. |
| 2010/0145343 A1 | 6/2010 | Johnson et al. |
| 2010/0145344 A1 | 6/2010 | Jordan et al. |
| 2010/0152782 A1 | 6/2010 | Stone et al. |
| 2010/0160917 A1 | 6/2010 | Fitz et al. |
| 2010/0168752 A1 | 7/2010 | Edwards |
| 2010/0168754 A1 | 7/2010 | Fitz et al. |
| 2010/0168857 A1 | 7/2010 | Hatch |
| 2010/0179663 A1 | 7/2010 | Steinberg |
| 2010/0185202 A1 | 7/2010 | Lester et al. |
| 2010/0191244 A1 | 7/2010 | White et al. |
| 2010/0212138 A1 | 8/2010 | Carroll et al. |
| 2010/0217109 A1 | 8/2010 | Belcher |
| 2010/0217270 A1 | 8/2010 | Polinski et al. |
| 2010/0217336 A1 | 8/2010 | Crawford et al. |
| 2010/0217338 A1 | 8/2010 | Carroll et al. |
| 2010/0228257 A1 | 9/2010 | Bonutti |
| 2010/0249657 A1 | 9/2010 | Nycz et al. |
| 2010/0249796 A1 | 9/2010 | Nycz |
| 2010/0262150 A1 | 10/2010 | Lian |
| 2010/0274253 A1 | 10/2010 | Ure |
| 2010/0281678 A1 | 11/2010 | Burdulis, Jr. et al. |
| 2010/0286700 A1 | 11/2010 | Snider et al. |
| 2010/0292743 A1 | 11/2010 | Singhal et al. |
| 2010/0305574 A1 | 12/2010 | Fitz et al. |
| 2010/0318088 A1 | 12/2010 | Warne et al. |
| 2010/0324692 A1 | 12/2010 | Uthgenannt et al. |
| 2011/0004317 A1 | 1/2011 | Hacking et al. |
| 2011/0009869 A1 | 1/2011 | Marino et al. |
| 2011/0015636 A1 | 1/2011 | Katrana et al. |
| 2011/0015639 A1 | 1/2011 | Metzger et al. |
| 2011/0015752 A1 | 1/2011 | Meridew |
| 2011/0022049 A1 | 1/2011 | Huebner et al. |
| 2011/0029091 A1 | 2/2011 | Bojarski et al. |
| 2011/0029116 A1 | 2/2011 | Jordan et al. |
| 2011/0035012 A1 | 2/2011 | Linares |
| 2011/0040303 A1 | 2/2011 | Iannotti |
| 2011/0040334 A1 | 2/2011 | Kaes et al. |
| 2011/0046735 A1 | 2/2011 | Metzger et al. |
| 2011/0054478 A1 | 3/2011 | Vanasse et al. |
| 2011/0066193 A1 | 3/2011 | Lang et al. |
| 2011/0066245 A1 | 3/2011 | Lang et al. |
| 2011/0071528 A1 | 3/2011 | Carson |
| 2011/0071529 A1 | 3/2011 | Carson |
| 2011/0071530 A1 | 3/2011 | Carson |
| 2011/0071532 A1 | 3/2011 | Carson |
| 2011/0071533 A1 | 3/2011 | Metzger et al. |
| 2011/0092804 A1 | 4/2011 | Schoenefeld et al. |
| 2011/0093086 A1 | 4/2011 | Witt et al. |
| 2011/0106254 A1 | 5/2011 | Abel et al. |
| 2011/0125264 A1 | 5/2011 | Bagga et al. |
| 2011/0151027 A1 | 6/2011 | Clineff et al. |
| 2011/0151259 A1 | 6/2011 | Jarman-Smith et al. |
| 2011/0153025 A1 | 6/2011 | McMinn |
| 2011/0160736 A1 | 6/2011 | Meridew et al. |
| 2011/0160867 A1 | 6/2011 | Meridew et al. |
| 2011/0166578 A1 | 7/2011 | Stone et al. |
| 2011/0172672 A1 | 7/2011 | Dubeau et al. |
| 2011/0184419 A1 | 7/2011 | Meridew et al. |
| 2011/0184526 A1 | 7/2011 | White et al. |
| 2011/0190899 A1 | 8/2011 | Pierce et al. |
| 2011/0190901 A1 | 8/2011 | Weissberg et al. |
| 2011/0213376 A1 | 9/2011 | Maxson et al. |
| 2011/0214279 A1 | 9/2011 | Park et al. |
| 2011/0218545 A1 | 9/2011 | Catanzarite et al. |
| 2011/0224674 A1 | 9/2011 | White et al. |
| 2011/0251617 A1 | 10/2011 | Ammann et al. |
| 2011/0257657 A1 | 10/2011 | Turner et al. |
| 2011/0269100 A1 | 11/2011 | Furrer et al. |
| 2012/0010619 A1 | 1/2012 | Barsoum |
| 2012/0010710 A1 | 1/2012 | Frigg |
| 2012/0010711 A1 | 1/2012 | Antonyshyn et al. |
| 2012/0101586 A1 | 4/2012 | Carson |
| 2012/0109137 A1 | 5/2012 | Iannotti et al. |
| 2012/0109226 A1 | 5/2012 | Iannotti et al. |
| 2012/0130382 A1 | 5/2012 | Iannotti et al. |
| 2012/0136365 A1 | 5/2012 | Iannotti et al. |
| 2012/0141034 A1 | 6/2012 | Iannotti et al. |
| 2012/0143267 A1 | 6/2012 | Iannotti et al. |
| 2012/0209276 A1 | 8/2012 | Schuster |
| 2012/0215225 A1 | 8/2012 | Philippon et al. |
| 2012/0232596 A1 | 9/2012 | Ribeiro |
| 2012/0271314 A1 | 10/2012 | Stemniski et al. |
| 2012/0289965 A1 | 11/2012 | Gelaude et al. |
| 2012/0296339 A1 | 11/2012 | Iannotti et al. |
| 2012/0303033 A1 | 11/2012 | Weiner et al. |

FOREIGN PATENT DOCUMENTS

| | | | |
|---|---|---|---|
| CA | 2505371 A1 | 5/2004 |
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1630495 A | 6/2005 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 3447365 A1 | 7/1986 |
| DE | 04219939 A1 | 12/1993 |
| DE | 4421153 A1 | 12/1995 |
| DE | 102009028503 A1 | 2/2011 |
| EP | 0114505 A1 | 8/1984 |
| EP | 0326768 A2 | 8/1989 |
| EP | 0579868 A2 | 1/1994 |
| EP | 0645984 A1 | 4/1995 |
| EP | 0650706 A1 | 5/1995 |
| EP | 0916324 A2 | 5/1999 |
| EP | 1321107 A1 | 6/2003 |
| EP | 1327424 A1 | 7/2003 |
| EP | 1437102 A1 | 7/2004 |
| EP | 01486900 A1 | 12/2004 |
| EP | 1852072 A2 | 7/2007 |
| EP | 1832239 A1 | 9/2007 |
| FR | 2659226 A1 | 9/1991 |
| FR | 2721195 A1 | 12/1995 |
| FR | 2768916 A1 | 4/1999 |
| GB | 2094590 A | 9/1982 |
| GB | 2197790 A | 6/1988 |
| GB | 2442441 A | 4/2008 |
| GB | 2447702 A | 9/2008 |
| JP | 59157715 A | 9/1984 |
| JP | 60231208 A | 11/1985 |
| KR | 20050072500 A | 7/2005 |
| KR | 20050084024 A | 8/2005 |
| RU | 2083179 C1 | 7/1997 |
| RU | 2113182 C1 | 6/1998 |

| | | |
|---|---|---|
| RU | 2125835 C1 | 2/1999 |
| RU | 2138223 C1 | 9/1999 |
| RU | 2175534 C2 | 11/2001 |
| RU | 2187975 C1 | 8/2002 |
| TW | 231755 | 5/2005 |
| WO | WO-8807840 A1 | 10/1988 |
| WO | WO-9107139 A1 | 5/1991 |
| WO | WO-9325157 A1 | 12/1993 |
| WO | WO-9528688 A1 | 10/1995 |
| WO | WO-9952473 A1 | 10/1999 |
| WO | WO-9959106 A1 | 11/1999 |
| WO | WO-0170142 A1 | 9/2001 |
| WO | WO-0184479 A1 | 11/2001 |
| WO | WO-0217821 A2 | 3/2002 |
| WO | WO-0226145 | 4/2002 |
| WO | WO-0236024 A1 | 5/2002 |
| WO | WO-02096268 A2 | 12/2002 |
| WO | WO-03051210 A2 | 6/2003 |
| WO | WO-03051211 A1 | 6/2003 |
| WO | WO-2004032806 A1 | 4/2004 |
| WO | WO-2004049981 A2 | 6/2004 |
| WO | WO-2004051301 A2 | 6/2004 |
| WO | WO-2004078069 A2 | 9/2004 |
| WO | WO-2005051239 A1 | 6/2005 |
| WO | WO-2005051240 A1 | 6/2005 |
| WO | WO-2005077039 A2 | 8/2005 |
| WO | WO-2006058057 A2 | 6/2006 |
| WO | WO-2006060795 A1 | 6/2006 |
| WO | WO-2006092600 A1 | 9/2006 |
| WO | WO-2006127486 A2 | 11/2006 |
| WO | WO-2006134345 A1 | 12/2006 |
| WO | WO-2006136955 A1 | 12/2006 |
| WO | WO-2007041375 A2 | 4/2007 |
| WO | WO-2007053572 A2 | 5/2007 |
| WO | WO-2007062079 A2 | 5/2007 |
| WO | WO-2007092841 A2 | 8/2007 |
| WO | WO-2007137327 A1 | 12/2007 |
| WO | WO-2007145937 A2 | 12/2007 |
| WO | WO-2008014618 A1 | 2/2008 |
| WO | WO-2008021494 A2 | 2/2008 |
| WO | WO-2008040961 A1 | 4/2008 |
| WO | WO-2008044055 A1 | 4/2008 |
| WO | WO-2008091358 A1 | 7/2008 |
| WO | WO-2008101090 A1 | 8/2008 |
| WO | WO-2008109751 A1 | 9/2008 |
| WO | WO-2008112996 A1 | 9/2008 |
| WO | WO-2008140748 A1 | 11/2008 |
| WO | WO-2009001083 A1 | 12/2008 |
| WO | WO-2009025783 A1 | 2/2009 |
| WO | WO-2009129063 A1 | 10/2009 |
| WO | WO-2009129067 A1 | 10/2009 |
| WO | WO-2010033431 A1 | 3/2010 |
| WO | WO-2010093902 A1 | 8/2010 |
| WO | WO-2010096553 A1 | 8/2010 |
| WO | WO-2010096557 A2 | 8/2010 |
| WO | WO-2010144705 A1 | 12/2010 |
| WO | WO-2010148103 A1 | 12/2010 |
| WO | WO-2011018458 A1 | 2/2011 |
| WO | WO-2011041398 A1 | 4/2011 |
| WO | WO-2011019797 A3 | 7/2011 |
| WO | WO-2011106711 A1 | 9/2011 |
| WO | WO-2011109260 A1 | 9/2011 |
| WO | WO-2012006444 A2 | 1/2012 |
| WO | WO-2012033821 A1 | 3/2012 |
| WO | WO-2012058344 A1 | 5/2012 |
| WO | WO-2012061042 A1 | 5/2012 |
| WO | WO-2012058353 A4 | 6/2012 |
| WO | WO-2012058355 A4 | 7/2012 |
| WO | WO-2012058349 A4 | 8/2012 |
| WO | WO-2012116206 A1 | 8/2012 |
| WO | WO-2012173929 A1 | 12/2012 |

OTHER PUBLICATIONS

International Search Report and Written Opinion mailed Mar. 5, 2012 for PCT/US2011/057300 claiming benefit of U.S. Appl. No. 12/938,905, filed Nov. 3, 2010.

International Search Report and Written Opinion mailed May 8, 2012 for PCT/US2012/026356 claiming benefit of U.S. Appl. No. 13/041,883, filed Mar. 7, 2011.

Thoma, W., et al., "Endoprothetischen Versorgung des Kniegelenks auf der Basis eines 3D-computertomographischen Subtraktionsverfahrens," Zuma Thema: Computergestützte orthopädische Chirugie, Der Orthopäde 29:641-644 Springer-Verlag (Jul. 2000) Translation provided: Thoma, W., "Endoprosthetic care of the knee joint based on a 3D computer chromatography subtraction process," Topic: Computer-aided orthopedic surgery. Orthopedist 2000 29:641-644 Springer Verlag (Jul. 2000).

Biomet "Oxford® Partial Knee" brochure, 8 pages (Feb. 2011).

Biomet "The Oxford® Partial Knee Surgical Technique," brochure, pp. 1-38, (Feb. 2010).

Biomet, "Oxfordt) Partial Knee Microplasty® Instrumentation Surgical Technique", brochure, pp. 1-54 (May 2011).

International Preliminary Report on Patentability and Written Opinion mailed Sep. 7, 2012 for PCT/US2011/026333 claiming benefit of U.S. Appl. No. 12/714,023, filed Feb. 26, 2010.

"Amazing Precision. Beautiful Results. The next evolution of MAKOplasty® is here," brochure. (Feb. 2009) MAKO Surgical Corp. 6 pages.

"Ascent Total Knee System," brochure. Biomet, Inc. (1999) 16 sheets.

"Customized Patient Instruments, Patient specific instruments for patient specific needs," brochure. (2008) DePuy Orthopaedics, Inc. 14 sheets.

"Customized Patient Instruments, Primary Cruciate Retaining Surgical Technique for use with the Sigma® Knee System Utilizing Specialist® 2 Instrumentation," brochure. (2008) DePuy Orthopaedics, Inc. pp. 1-23.

"Discovery® Elbow System Surgical Technique," brochure. Biomet Orthopedics, Inc. (2008) pp. 1-25.

"Discovery® Elbow System," brochure. Biomet Orthopedics, Inc. (2007) 3 sheets.

"Hipsextant Instructions of Use." (2011) Surgical Planning Associates, Inc. 19 pages.

"Knee tensor combined with laser femoral head locator," Research Disclosure. Jul. 2006. No. 507; p. 903.

"Method for constructing an allograft sleeve." Research Disclosure (Dec. 2003) No. 476, p. 1294.

"OSS™ Orthopaedic Salvage System, Femoral/Tibial Augmentation," brochure. Biomet Orthopedics, Inc., (2003) pp. 1-8 (12 sheets).

"Patient Matched PMI Implants, C.A.M.R.A. 3-D Imaging," brochure, Biomet, Inc. (1990) 6 pages.

"Regenerex® Tibial Cone Augment, Surgical Technique Addendum to the Vanguard® SSK Revision System," brochure. Biomet® Orthopedics. (2009) pp. 1-8 (12 sheets).

"Signature™ Personalized Patient Care, Surgical Technique Addendum to the Vanguard Knee System" brochure. Biomet® Orthopedics, Inc. (2009) pp. 1-8.

"TruMatch™ Personalized knee replacement solutions," tri-fold brochure. (2009) SIGMA® DePuy Orthopaedics, Inc. 2 pages.

"Vanguard® PFR Partial Knee Patellofemoral Replacement System," Surgical Technique brochure. Biomet Orthopaedics, (2010) pp. 1-25.

"Zimmer® UniSpacer® Knee System," brochure. (2005) Zimmer, Inc. 4 sheets.

Birnbaum, Klaus, M.D., "Computer-Assisted Orthopedic Surgery With Individual Templates and Comparison to Conventional Method," SPINE vol. 26, No. 4, pp. 365-370 (2001) Lippincott Williams & Wilkins, Inc.

Botha, Cherl P., Technical Report: DeVIDE—The Delft Visualisation and Image processing Development Environment, pp. 1-49 (May 31, 2006).

Cohen, Zohara A., et al. "Knee cartilage topography, thickness, and contact areas from MRI: in-vitro calibration and in-vivo measurements." Journal of the OsteoArthritis Research Society International. Osteoarthritis and Cartilage, (1999) vol. 7; No. 1 pp. 95-109.

Eckhoff, Donald G., et al., "Three-Dimensional Mechanics, Kinematics, and Morphology of the Knee Viewed in Virtual Reality," The Journal of Bone & Joint Surgery, vol. 81 (Dec. 4, 2005) pp. 71-80.

Fortin, Thomas, D.D.S., Ph.D., et al., "Precise Dental Implant Placement in Bone Using Surgical Guides in Conjunction with Medical Imaging Techniques," Journal of Oral Implantology, Clinical, vol. 26, No. 4 (2000) pp. 300-303.

Haaker, R.G., et al., "Minimal-invasive navigiert implantierte unikondyläre Knieendoprothese," Orthopäde 2006 35:1073-1079 (2006) Spinger Medizin Verlag.

Hafez, M.A., et al., "Computer-assisted Total Knee Arthroplasty Using Patient-specific Templating," Clinical Orthopaedics and Related Research, No. 444 (pp. 184-192) 2006 Lippincott Williams & Wilkins.

Hazen, Eric J., M.D., "Computer-Assisted Orthopaedic Sugery, A New Paradigm," Techniques in Orthopaedics® vol. 18, No. 2, (2003) pp. 221-229.

Hutmacher, Dietmar, W., "Scaffolds in tissue engineering bone and cartilage," Biomaterials, 2000 Elsevier Science Ltd. (pp. 2529-2543).

International Preliminary Report on Patentability and Written Opinion for PCT/US2009/039578 mailed Oct. 28, 2010 claiming benefit of U.S. Appl. No. 12/103,834, filed Apr. 16, 2008.

International Preliminary Report on Patentability and Written Opinion mailed Oct. 28, 2010 for PCT/US2009/039507 claiming benefit of U.S. Appl. No. 12/103,824, filed Apr. 16, 2008.

International Preliminary Report on Patentability for PCT/US2007/013223 mailed Dec. 24, 2008 claiming benefit of U.S. Appl. No. 11/756,057, filed May 31, 2007.

International Preliminary Report on Patentability mailed Mar. 31, 2011 for PCT/US2009/056670 claiming benefit of U.S. Appl. No. 12/211,407, filed Sep. 16, 2008.

International Search Report and Written Opinion for PCT/US2007/013223 mailed Nov. 26, 2007, claiming benefit of U.S. Appl. No. 11/756,057, filed May 31, 2007.

International Search Report and Written Opinion for PCT/US2009/039507 mailed Jul. 14, 2009, claiming benefit of U.S. Appl. No. 12/103,824.

International Search Report and Written Opinion for PCT/US2009/056670 mailed Mar. 2, 2010 claiming benefit of U.S. Appl. No. 12/211,407, filed Sep. 16, 2008.

International Search Report and Written Opinion mailed Apr. 22, 2010 for PCT/US2010/024579 claiming benefit of U.S. Appl. No. 12/389,930, filed Feb. 20, 2009.

International Search Report and Written Opinion mailed Aug. 19, 2010 for PCT/US2010/024584 claiming benefit of U.S. Appl. No. 12/389,901, filed Feb. 20, 2009.

International Search Report and Written Opinion mailed Dec. 7, 2010 for PCT/US2010/050701 claiming benefit of U.S. Appl. No. 12/571,969, filed Oct. 1, 2009.

International Search Report and Written Opinion mailed Jul. 31, 2009 for PCT/US2009/039578 claiming benefit of U.S. Appl. No. 12/103,834, filed Apr. 16, 2008.

International Search Report and Written Opinion mailed Jun. 10, 2010 for PCT/US2010/038177 claiming benefit of U.S. Appl. No. 12/483,807, filed Jun. 12, 2009.

International Search Report and Written Opinion mailed Jun. 4, 2010 for PCT/US2010/024073 filed Feb. 12, 2010, claiming benefit of U.S. Appl. No. 12/371,096, filed Feb. 13, 2009.

International Search Report and Written Opinion mailed May 9, 2011 for PCT/US2011/026412 claiming benefit of U.S. Appl. No. 12/872,663, filed Aug. 31, 2010.

International Search Report and Written Opinion mailed Oct. 5, 2010 for PCT/US2010/038845 claiming benefit of U.S. Appl. No. 12/486,992, filed Jun. 18, 2009.

Invitation to Pay Additional Fees mailed May 3, 2011 for PCT/US2011/026333 claiming benefit of U.S. Appl. No. 12/714,023, filed Feb. 26, 2010.

Invitation to Pay Additional Fees with Partial International Search mailed Nov. 26, 2009 for PCT/US2009/056670.

Kaus, Michael R., Ph.D., "Automated Segmentation of MR Images of Brain Tumors," Radiology, vol. 218, No. 2, (2001) pp. 586-591.

Kelly, Todd C., M.D., "Role of Navigation in Total Hip Arthroplasty." The Journal of Bone & Joint Surgery(2009) pp. 153-8. vol. 91-A, Supplement 1.

Klein, M., "Robot assisted insertion of craniofacial implants—clinical experience," CARS 2001, pp. 133-138 (2001) Elsevier Science B.V.

Lombardi, Adolph, et al., "Patient-Specific Approach in Total Knee Arthroplasty," Knee Orthopedics, ORTHOSuperSite (Sep. 1, 2008), 5 pages, http://www.orthosupersite.com/view.aspx?rid=31419, printed May 20, 2010.

Lynch, John A., et al., "Cartilage segmentation of 3D MRI scans of the osteoarthritic knee combining user knowledge and active contours," Medical Imaging 2000: Image Processing SPIE vol. 3979 (2000) pp. 925-935.

Murphy, S.B., et al. "The Hip Sextant: Navigation of Acetabular Component Orientation Using a Mechanical Instrument," brochure. (2009) 1 page.

Nicholls, Paul, M.D., "Trauma Grand Rounds PMI (Patient-Matched Implants)" brochure, Biomet Orthopedics, Inc., (Feb. 29, 2000) 1 page.

Overhoff, H.M., et al., "Total Knee Arthroplasty: Coordinate System Definition and Planning based on 3-D Ultrasound Image Volumes," CARS 2001, pp. 283-288, (2001) Elsevier Science B.V.

Portheine, F., "CT-basierte Planung und DISOS-Schablonennavigation in der Kniegelenkendoprothetik," in Navigation und Robotic in der Gelenk—und Wirbelsäulenchirugie, Kapitel 32, Springer Verlag (2003) pp. 262-269.

Portheine, F., et al., Entwicklung eines klinischen Demonstrators für die computerunterstützte Orthopädische Chirurgie mit CT-Bildbasierten Individualschablonen, Bildverarbeitung fur die Medizin (1998) 5 pages.

Portheine, K., "Development of a clinical demonstrator for computer assisted orthopedic surgery with CT-image based individual templates," Computer Assisted Radiology and Surgery, pp. 944-949, (1997) Elsevier Science B.V.

Radermacher, "Computer Assisted Orthopaedic Surgery with Image Based Individual Templates," Clinical Orthopaedics and Related Research No. 354, pp. 28-38 (1998) Lippincott Williams & Wilkins.

Radermacher, K., et al., "Computer Integrated Orthopaedic Surgery: Connection of Planning and Execution in Surgical Intervention," Computer-integrated surgery: technology and clinical applications, (1996) pp. 451-463.

Radermacher, K., et al., "CT Image-Based Planning and Execution of Interventions in Orthopedic Surgery Using Individual Templates, Experimental Results and Aspects of Clinical Applications," Computer Assisted Orthopedic Surgery (CAOS), pp. 42-52, (1995) Hogrefe & Huber Publishers.

Radermacher, K., et al., "Image Guided Orthopedic Surgery Using Individual Templates," Springer Berlin/Heidelberg, CVRMed-MRCAS'97, vol. 1205/1997 pp. 606-615).

Radermacher, K., et al., "Technique for Better Execution of CT Scan Planned Orthopedic Surgery on Bone Structures," Supplied by the British Library—"The world's knowledge" 2nd Congress of ISCAS Conference in Berlin Germany (Jun. 1995) pp. 933-938.

Radermacher, Klaus, et al. "Computer Assisted Orthopaedic Individual Templates." Clinical Orthopaedics and Related Research. (Sep. 1998) No. 354; pp. 28-38.

Schuller-Götzburg, P., et al., 3D-Implantatplanung and Stereolithographie-Implantatbohrschablonen, Stomatologie 101.3, pp. 55-59 (2004).

Sharp, S. Michael, Ph.D., Patient-Specific, Resurfacing Bi-Compartmental Arthuroplasty, Futuretech, Orthopaedic Product News (Mar./Apr. 2008) pp. 12-15.

Sisto, Domenick, J., et al., "Custom Patellofemoral Arthroplasty of the Knee Surgical Technique," Journal of Bone and Joint Surgery, vol. 89-A, pp. 214-225 (2007).

Slammin, John et al, "Do You Have This Implant in My Size?", MDT Medical Design Technology, 3 pages, http://www.mdtmag.com/scripts/ShowPR.asp?PUBCODE=046&ACCT=0007796&ISSUE .. . accessed Jul. 31, 2008.

Steinwachs, Matthias Reinhard, "Cartilage Repair—Autologous Chondrocyte Transplantation and Autologous Matrix-induced Chondrogenesis," European Musculoskeletal Review (2006) pp. 65-68.

International Preliminary Report on Patentability mailed Aug. 25, 2011 for PCT/US2010/024073 filed Feb. 12, 2010, claiming benefit of U.S. Appl. No. 12/371,096, filed Feb. 13, 2009.

International Preliminary Report on Patentability mailed Sep. 1, 2011 for PCT/US2010/024579 claiming benefit of U.S. Appl. No. 12/389,930, filed Feb. 20, 2009.

International Preliminary Report on Patentability mailed Sep. 1, 2011 for PCT/US2010/024584 claiming benefit of U.S. Appl. No. 12/389,901, filed Feb. 20, 2009.

International Search Report and Written Opinion mailed Aug. 9, 2011 for PCT/US2011/026333 claiming benefit of U.S. Appl. No. 12/714,023, filed Feb. 26, 2010.

Great Britain Search Report mailed Dec. 21, 2011 for GB1116054.6, claiming benefit of U.S. Appl. No. 12/888,005, filed Sep. 22, 2010.

International Preliminary Report and Written Opinion mailed Jan. 5, 2012 for PCT/US2010/038845 claiming benefit of U.S. Appl. No. 12/486,992, filed Jun. 18, 2009.

International Preliminary Report on Patentability and Written Opinion mailed Dec. 22, 2011 for PCT/US2010/038177 claiming benefit of U.S. Appl. No. 12/483,807, filed Jun. 12, 2009.

International Search Report amiled Nov. 30, 2010 for PCT/EP2010/061630 filed Aug. 10, 2010 claiming benifit of DE102009028503.2 filed Aug. 13, 2009.

Supplementary European Search Report mailed Nov. 15, 2011 for EP07809326, which claims benefit of PCT/US2007/013223, filed Jun. 5, 2007; which claims priority to U.S. Appl. No. 11/756,057, filed May 31, 2007.

International Search Report and Written Opinion mailed Nov. 15, 2012, for PCT/US2012/052853, which claims benefit of U.S. Appl. No. 13/221,968, filed Aug. 31, 2011.

International Search Report and Written Opinion mailed Dec. 18, 2012 for PCT/US2012/059189, which claims benefit of U.S. Appl. No. 13/597,478, filed Aug. 29, 2011.

* cited by examiner

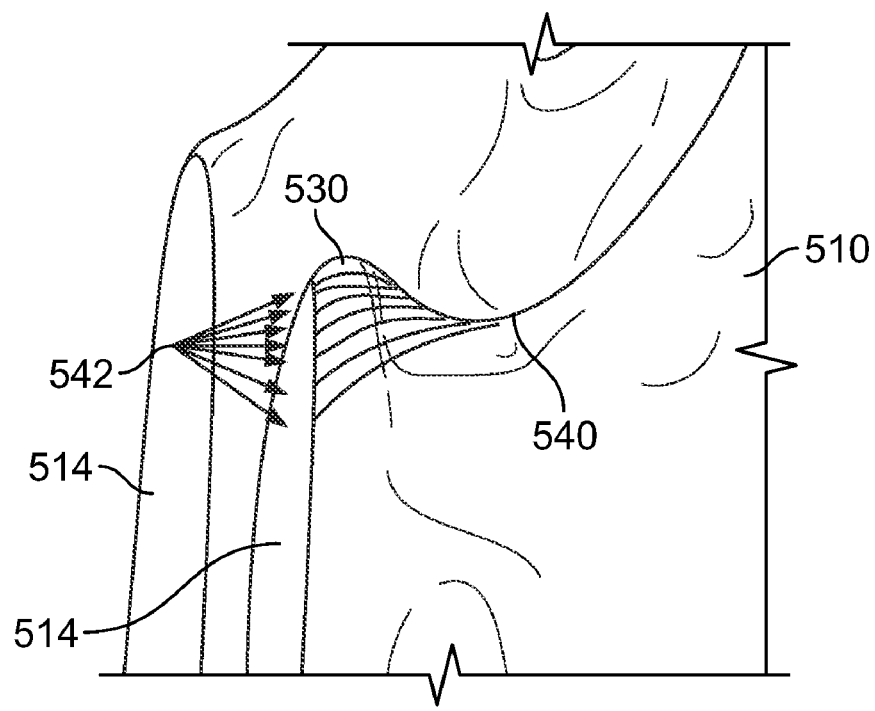
FIG. 10
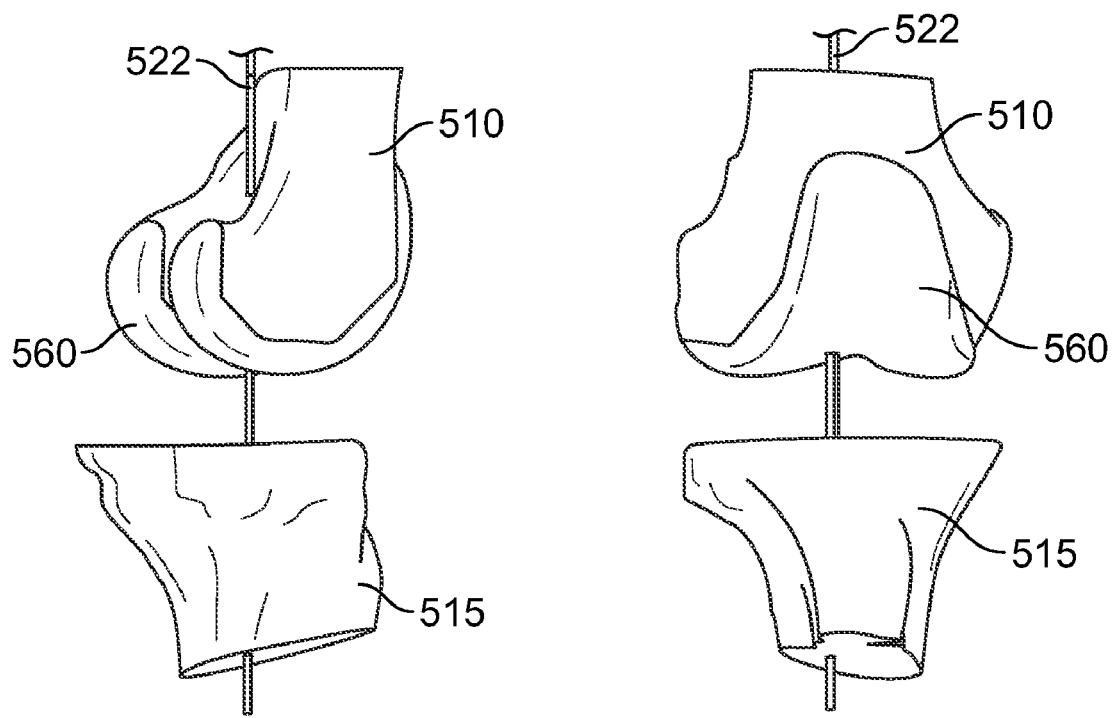
FIG. 11  FIG. 12

METHOD AND APPARATUS FOR MANUFACTURING AN IMPLANT

CROSS-REFERENCE TO RELATED APPLICATIONS

This application claims the benefit of U.S. Provisional Application No. 61/310,752 filed on Mar. 5, 2010.

This application is a continuation-in-part of U.S. application Ser. No. 12/483,807, filed on Jun. 12, 2009, which is a continuation-in-part of U.S. application Ser. No. 12/371,096, filed on Feb. 13, 2009, which is a continuation-in-part of U.S. application Ser. No. 12/103,824, filed on Apr. 16, 2008, which claims the benefit of U.S. Provisional Application No. 60/912,178, filed on Apr. 17, 2007.

This application is also a continuation-in-part of U.S. application Ser. No. 12/103,834, filed on Apr. 16, 2008, which claims the benefit of U.S. Provisional Application No. 60/912,178, filed on Apr. 17, 2007.

The disclosures of all the above applications are incorporated herein by reference.

INTRODUCTION

The present teachings provide an implant customized for a specific patient based on a plurality of parameters identified during a preoperative planning stage.

SUMMARY

The present teachings provide an orthopedic device that includes a femoral implant having a non-custom internal bone engagement surface. The femoral implant further includes at least nine parameters adjusted preoperatively to correspond to a specific patient. In one embodiment, the femoral implant includes three patient-specific lengths, three patient specific medial angles and three patient specific lateral angles, wherein the lengths and medial and lateral angles are selected preoperatively based on a three-dimensional image of an anatomy of a patient to match the anatomy of the patient.

The present teachings provide an orthopedic device manufacturing method. In one embodiment, the method includes preparing a three-dimensional image of a patient's joint, selecting a non-custom implant closely matching the joint, and modifying at least six angles of the implant to be patient-specific. In another embodiment, the method includes preparing a three-dimensional image of a patient's joint, selecting a non-custom femoral implant closely matching the joint, and modifying at least three lengths and six angles of the femoral implant to be patient-specific.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein:

FIG. 10 is a representative image of a patent's anatomy showing representative depth control selections for surgeon manipulation;

FIGS. 11 and 12 are representative images of a patent's anatomy after osteophyte/protrusion removal with exemplary implants attached thereon;

DESCRIPTION OF VARIOUS ASPECTS

The following description is merely exemplary in nature and is in no way intended to limit the present teachings, applications, or uses. For example, although some of the present teachings are illustrated for a knee implant, the present teachings can be used for any orthopedic implant.

The present teachings provide a manufacturing method that integrates patient's anatomic and medical information with interactive participation by a surgeon to select and manufacture an implant and, optionally, related surgical instruments, for a particular patient from generally three options: a custom made implant specific to the patient, an implant that is only partially custom-made or a semi-custom implant, and a standard off-the shelf implant. Similarly, off-the-shelf, custom-made, or semi-custom-made instrumentation (e.g. alignment guides, drill guides, cutting guides or other instruments) can be selected and manufactured, as recommended by the surgeon, for the surgical procedure. All the implant components, alignment guides, and other disposable instruments can be included in a package provided to a surgeon for a specific patient.

Figure 1:
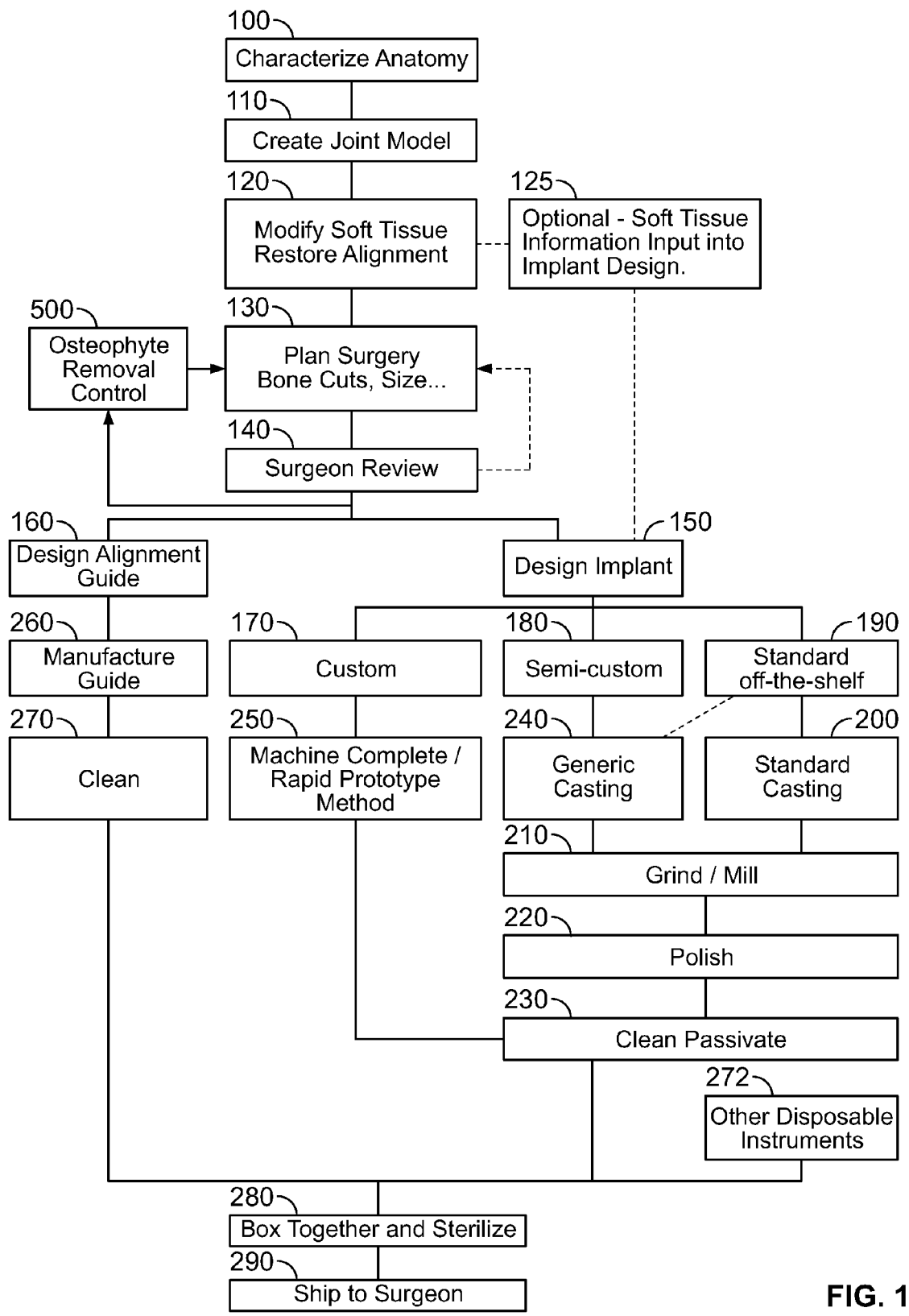
FIG. 1 is a flowchart of an implant manufacturing method according to the present teachings.

Referring to FIG. 1, an exemplary flowchart of an interactive implant manufacturing method according to the present teachings is illustrated. The portion of the patient's anatomy related to the orthopedic procedure and the implant is characterized and detailed at 100. The characterization can be performed with various imaging methods capable of obtaining a representation of the affected anatomy, including, for example, soft and hard tissues. The tissues can include bone, bone joints with or without cartilage, ligaments, or other soft tissue. The imaging methods can include, for example, MRI, CT, ultrasound, radiography or X-ray, cameras and other devices.

The image information for the patient can be obtained at a medical facility or a doctor's office and can be sent to the manufacturer in an electronic and/or digital form contained. The image information can be stored on a physical medium, such as a CD, DVD, flash memory device (e.g. memory stick, compact flash, secure digital card), or other storage device. The information may alternatively, or in addition, be transmitted electronically with the Internet or worldwide web using appropriate transfer protocols. Also, electronic transmissions can include e-mail or other digital transmission to any appropriate type of computer device, smart phone, PDA or other devices in which electronic information can be transmitted.

Appropriate handheld devices (used as illustrated in FIG. 13), can include handheld mobile device or portable communication devices, such as the iPhone® handheld mobile device sold by Apple Inc., a corporation of California, USA; the LG Shine® handheld mobile device sold by LG Corp. a corporation of REPUBLIC OF KOREA; or the Blackberry Bold® handheld mobile device sold by Research In Motion Limited a corporation of CANADA. The handheld device can be those that are held in the palm of a hand of a user, such as a surgeon (see FIG. 14). The surgeon can then enter data with a stylus, keyboard, touch screen, etc. The handheld device can use local area networks, cell phone networks, or other data transmission systems to communicate with a main memory and processor of a service provider (see FIG. 14).

Appropriate handheld devices can provide access to electronic communication or file transfer protocols, such as internet or electronic mail, to transfer or access information files. The handheld devices can have installed programs that can be used to manipulate the information files, as discussed herein. Alternatively, or in addition thereto, the handheld devices can access servers that process data files while receiving input through the handheld devices and displaying images to the surgeon or user via the handheld device. In certain instances, the handheld device may only be a client that does not process and edit a data file of the pre-operative plan.

With continued reference to FIG. 1, at 110, the information collected at 100 can be used to create a three-dimensional model or image of the bone or joint with or without associated soft tissue or related anatomy using commercially available computer modeling software from various vendors or developers, such as, for example, from Materialise USA, Ann Arbor, Mich. The three-dimensional model of the patient's anatomy can be viewed on a computer display or other electronic screen and can also reproduced as a hard copy on film or other medium and viewed by direct or indirect or backlight illumination. The model can be sized for viewing on any appropriate screen size and may be cropped, rotated, etc. as selected by the individual (e.g. the surgeon) viewing the screen.

At 120, soft tissue associated with the affected anatomy can be modified, or removed or repaired, to restore alignment of the joint, for example, or to remove torn or diseased tissue, or to cut or repair ligaments, or to provide natural or artificial ligament grafts. Soft tissue information can be optionally used as an additional design parameter or input for the implant design, at 125. For example, a custom or patient-specific bearing articulation of a knee joint can be designed based on the kinematic profile and the soft tissue/ligament information available for a particular patient. Further, kinematic information for the patient can be obtained by an actual gait analysis of the patient, and can also be obtained by computer modeling software that uses the MRI images of the patient's joints and associated ligaments, muscle or other soft tissue to derive kinematic analysis of the patient and corresponding recommendations for soft tissue modification, such as releasing a ligament, for example. Such software is commercially available from LifeModeler, Inc., of San Clemente, Calif.

At 130, a preliminary pre-operative plan of the surgical procedure can be prepared for surgeon or other medical user or technician review, including the planning of various bone resections, sizes and types of implants, and various geometric requirements including relevant dimensions, such as height, width, orientation of particular features, etc. The preliminary pre-operative surgical plan can include a recommendation of particular implants and associated instruments to be used in the surgical procedure, as discussed below. The preliminary pre-operative surgical plan can be in the form of digital images that can be viewed interactively using a computer modeling software, such as the software referenced above. The preliminary pre-operative plan and any further changes or a finalized pre-operative plan can be a plan devised to obtain a healthy or as close to healthy anatomical orientation after an operative procedure. The healthy anatomy can be based on natural or pre-injury anatomy or mechanically correct or efficient anatomical orientation.

At 140, the preliminary pre-operative surgical plan can be submitted to the surgeon (or other user) for review, either electronically or by land mail, and either in digital or hard copy form, as discussed above in connection with transmitting imaging information. In particular, the surgeon can review the resection planes shown in image of the patient's anatomy, make changes in the location, size and orientation of the resection planes and, generally, work interactively until the pre-operative plan from 130 is surgeon-approved. Specifically, the surgeon may approve the image of the patient's anatomy showing corresponding resection planes. As shown in FIGS. 7 and 8, the patient's anatomy 510, as represented in the image, can be, for example, a distal femur with approved resection planes including medial and lateral anterior chamfer planes 513, medial and lateral anterior cut planes 511, medial and lateral posterior chamfer planes 512 and medial and lateral posterior cut planes 514. Following the surgeon's approval of the anatomy and the resection planes at 140, the surgeon is provided with the opportunity to remove one or more osteophytes/protrusions from the image of the patient's anatomy 510 at surgeon-selected locations and depths at 500 (See FIG. 6). Removal of such protrusions and smoothening of the joint surface that receives the implant can parallel the intra-operative joint preparation by the surgeon and improve the actual fit of a surgeon-selected implant, whether patient-specific, semi custom, or off the shelf.

An automated osteophyte/protrusion removal control module 500 can be incorporated in the planning stage of the manufacturing method illustrated in FIG. 1. The automated osteophyte/protrusion removal control module 500 can be provided as a separate pre-operative planning module, as shown in FIG. 6, or it can be incorporated and/or fully integrated with the manufacturing method illustrated in FIG. 1.

Certain parts of the bone, including various bone bumps, protrusions, growths and osteophytes can be generally removed from the three-dimensional reconstruction of a patient's anatomy before designing a patient-specific implant or semi-custom implant, or before selecting an off the shelf implant. The automated osteophyte/protrusion removal control module can replace a time-consuming and potentially less accurate manual modification of the three-dimensional image to remove such bone growths or osteophytes by an experienced image or CAD technician. The automated osteophyte/protrusion removal control module 500 can provide more accurate and faster removal of such bone irregularities, which can vary in shape, location and size from patient to patient. It will be appreciated that the osteophyte/protrusion removal control module 500 can be used for smoothing out a bone surface by removing any type of bone protrusion, including bumps, irregularities and osteophytes. According to the present teachings, osteophytes are illustrated as exemplary, but not exclusive, candidates for complete or partial removal.

Figure 6:
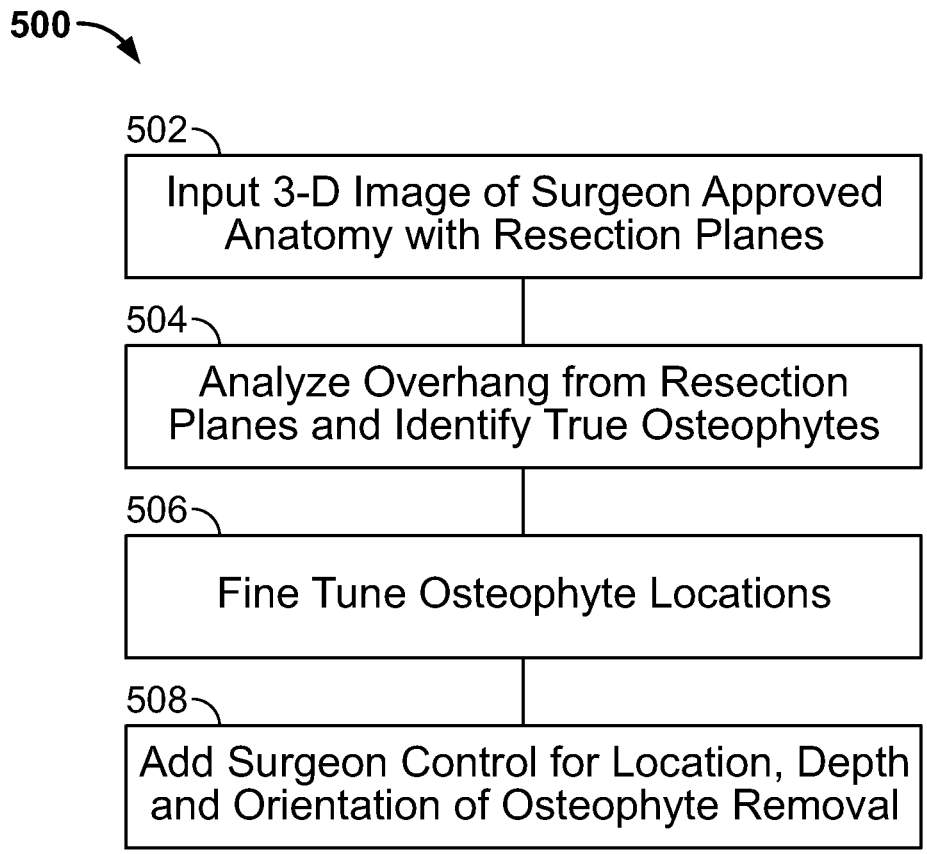
FIG. 6 is a flow chart for an osteophyte/protrusion removal control method according to the present teachings.
Figure 7:
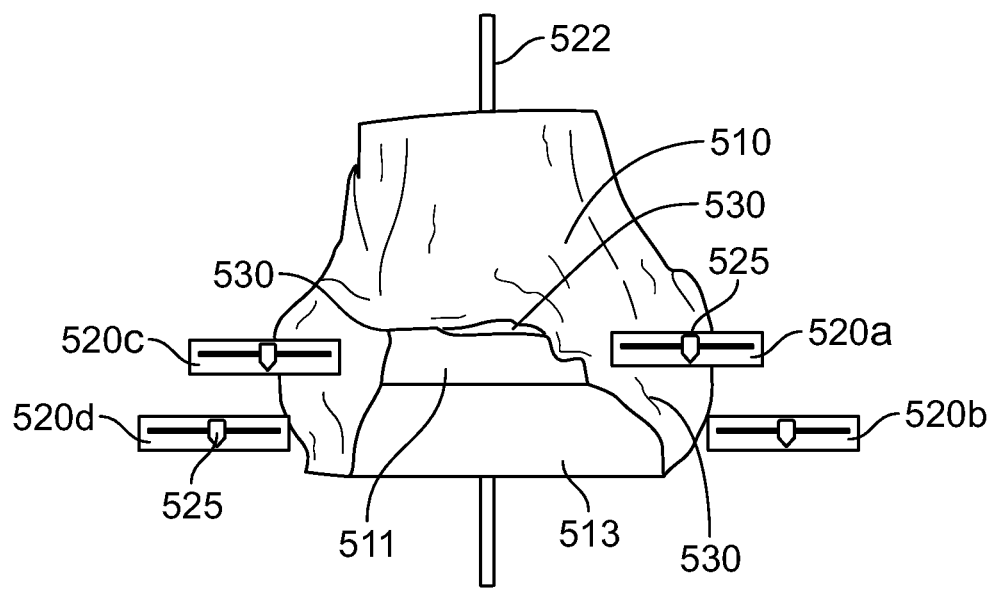
FIG. 7 is a representative image of a patent's anatomy showing osteophyte/protrusion control tools for modifying the image.
Figure 8:
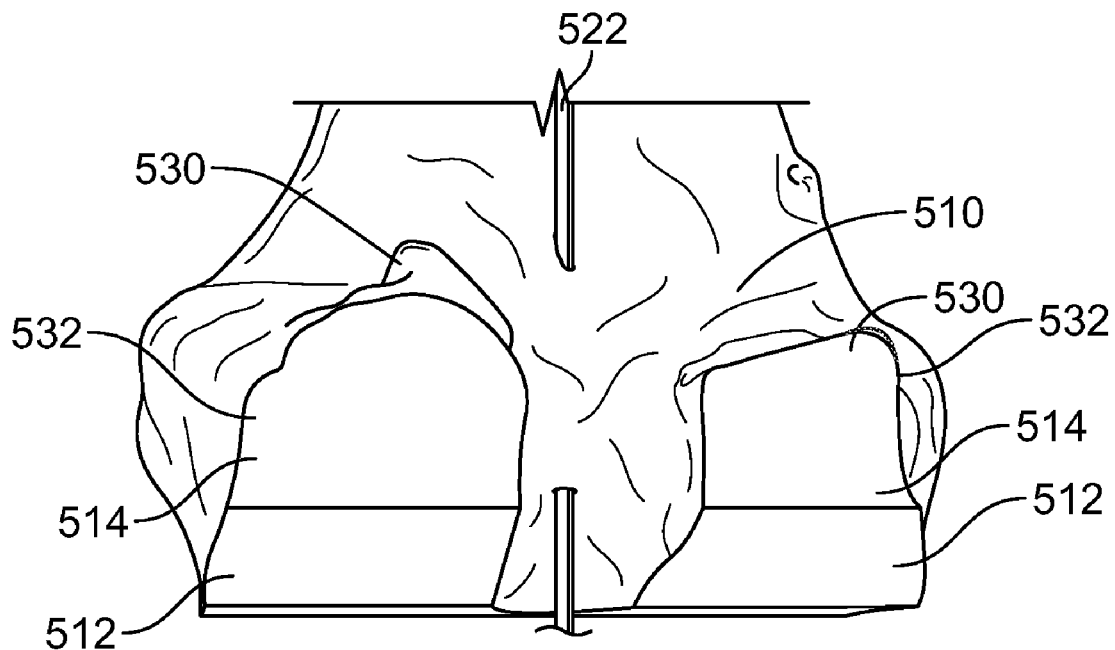
FIGS. 8 and 9 are representative images of a patent's anatomy showing exemplary osteophyte/protrusion locations.
Figure 9:
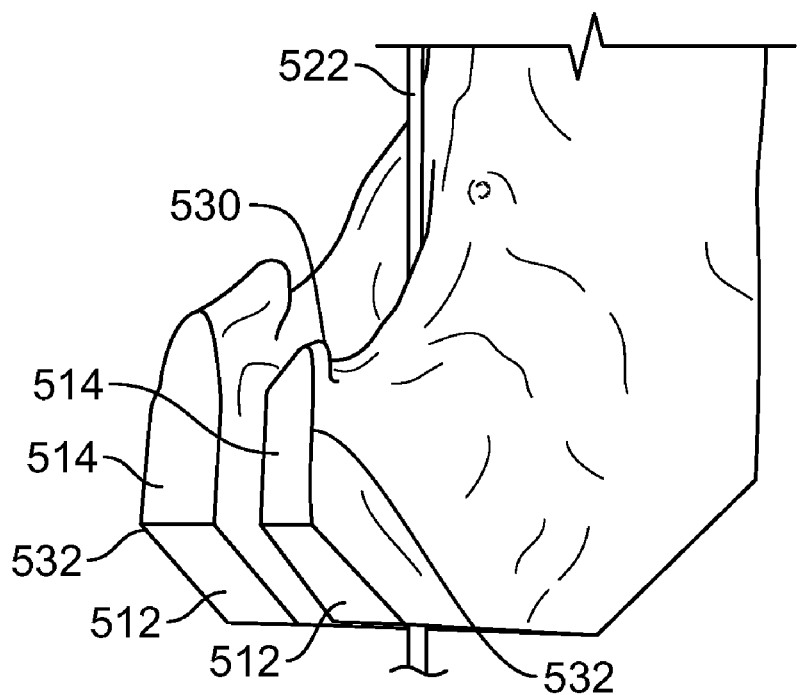

Referring to FIG. 6, the osteophyte/protrusion removal control module 500 can start 502 with an input of the three-dimensional image of the patient's anatomy 510 including resection planes, as shown in FIGS. 7-9, after review and approval of the resection planes by the surgeon (or other user, including other professionals or technicians) at 140 of FIG. 1. In the exemplary illustration of FIG. 7, the image of the patient's anatomy 510 can be analyzed to identify osteophyte/protrusion locations 530 (at 504 of FIG. 6) by determining tissue or bone overhang protruding past outer edges 532 of the various resection planes, such as the resection planes illustrated at 511, 513, 512 and 514 in FIGS. 7-9. If such osteophyte/protrusions 530 extend beyond the edges of the resection planes in the direction of the planned or anticipated implant location, the osteophyte/protrusions 530 can interfere with implant fitting.

Referring to FIGS. 6, 7 and 10, in addition to identifying the location of osteophytes/protrusions 530, the osteophyte/protrusion removal control module 500 can provide visual control for the surgeon to select the aggressiveness of osteophyte/protrusion removal, or the degree of smoothening and/or flattening of the corresponding joint anatomy. Specifically, by fine-tuning the osteophyte/protrusion locations, at 506 of FIG. 6, the surgeon can control the depth of the osteophyte/protrusion removal in a continuous or discrete manner. In one aspect, a landmark location 540 for each osteophyte/protrusion 530 can be identified and pegged for measuring from and initiating a continuous series of constant or variable depth contours 542 to aid the surgeon in selecting the depth of osteophyte/protrusion removal. The depth contours can be automatically generated by the computer software that generates a three-dimensional model or image of the anatomy, such as the software commercially available, for example, from Materialise USA, Ann Arbor, Mich. The landmark location 540 can be a location of lowest possible depth in the vicinity of the identified osteophyte/protrusion, a minimum, or a valley location, as shown in FIG. 10. Although the depth contours 542 are shown as discrete in FIG. 10, it will be appreciated that a continuous removal control can be provided, such that the surgeon can exercise unlimited choices of depth contours for removal. The depth contours 542 can represent curved smoothed-out surfaces under the original osteophyte/protrusion 530 and can be exposed after an overlying area is shaved or peeled in the image of the patient's anatomy 510 by the operation of graphical or visual removal tools provided on the image of the patient's anatomy 510. The surgeon or other user can manipulate the graphical removal tools with a user interface, such as a mouse, touch screen, joystick, slide pad, or other user interface.

Referring to FIG. 7, various visual removal tools can be provided for on-screen manipulation and control by the surgeon, at 508 of FIG. 6. For example, a removal tool corresponding to each edge of a resection plane can be provided and used to visually/graphically remove a portion of an osteophyte/protrusion associated with a particular edge 532. In FIG. 7, four such exemplary removal tools 520a, 520b, 520c, 520d (collectively referenced as 520) are shown, each removal tool associated with an edge of a resection plane, such as lateral and medial chamfer plane and lateral and medial cut plane. Although the removal tools 520 are illustrated as straight sliders in FIG. 7, the amount removed follows a depth contour 542, as illustrated in FIG. 10. The removal tools 520 can include a visual indicator 525 that can provide information to the surgeon in the form of a number on a scale indicative of the depth of aggressiveness of osteophyte/protrusion removal. In another aspect, the indicator 525 can provide visual information in terms of variable color in shades gradually changing from minimum depth removal (green, for example) to maximum depth removal (red, for example).

After the surgeon completes the osteophyte/protrusion removal, the surgeon can manipulate and superimpose implant images in relation to the modified patient's anatomy 510. In FIGS. 11 and 12, exemplary images of a resected femur 510 and tibia 515 referenced relatively to a mechanical axis 522 are illustrated. The femur image illustrates the patient's anatomy 510 after the osteophytes/protrusions 530 shown in FIGS. 8 and 9 have been removed and a femoral implant/component 560 is placed on the resulting smoothed out surface that follows one of the depth contours 542 shown in FIG. 9.

Figure 1A:
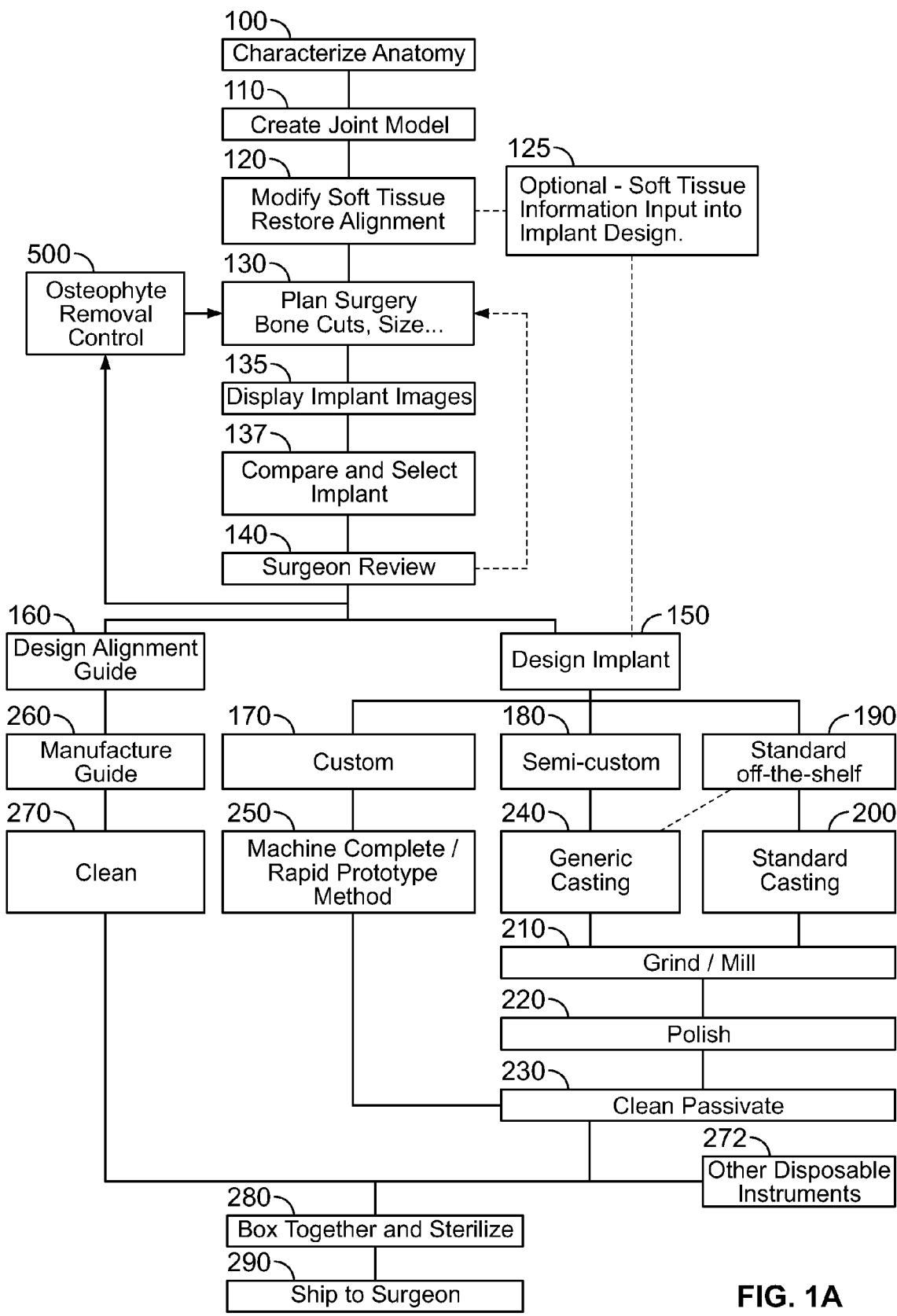
FIG. 1A is a flowchart of an implant manufacturing method according to the present teachings.
Figure 1B:
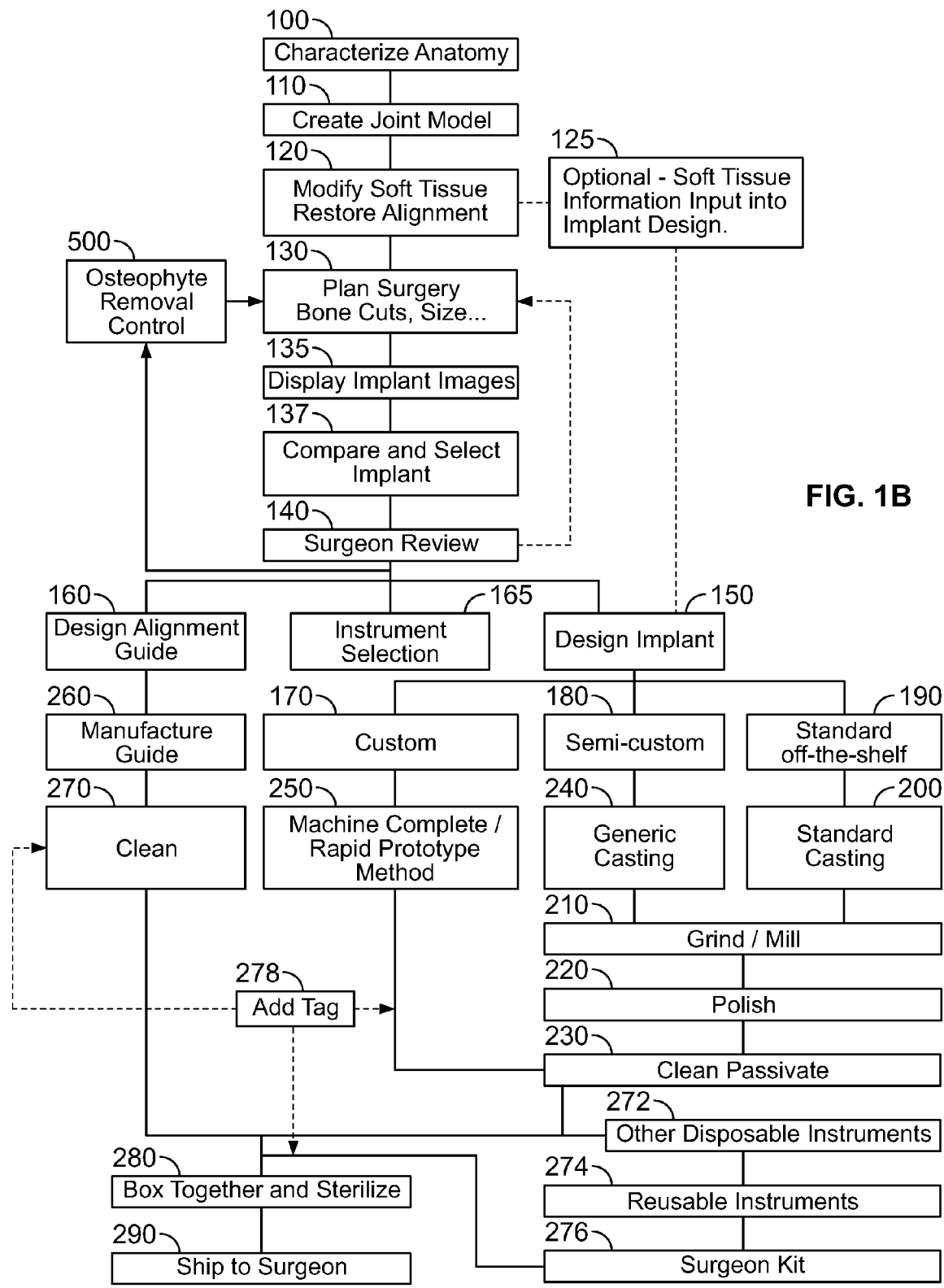
FIG. 1B is a flowchart of an implant manufacturing method according to the present teachings.

Referring to FIGS. 1, 1A, and 1B, based on the preliminary pre-operative surgical plan and the patient information, the surgeon can make a recommendation regarding the design of the implant at 150, and any desired associated alignment guides at 160. At 150, the surgeon can recommend a method of designing an implant. Specifically, the surgeon can select one of the following three options: a first option of a custom or patient-specific implant at 170 or a second option of a semi-custom made implant at 180, or a third option of a standard or off-the-shelf implant at 190. The surgeon can also include recommendations and preferences for various custom and non custom instruments to be used in the procedure at the surgeon review at 140, as well as at the selection and design of implant at 150 and selection and design of alignment guides 160. It will be appreciated that, based on the surgeon's recommendation at 140, the preliminary pre-operative surgical plan can be modified at 130, including all the surgeon's preferences regarding anatomy modification (osteophyte removal, resection planes, etc), implant design, alignment guide design and selection of various tools and instruments, and then resubmitted to the surgeon for approval.

A custom-made implant is a patient-specific, one of a kind implant specifically made for a particular patient, and consequently there is no inventory associated with such implant. Standard or off-the-shelf-implants are available and stocked in a number of sizes, typically six or more, and a number of configurations or types, including bilateral or unilateral implants, constrained, semi-constrained, mobile, etc. Because of the variety of sizes and configurations that are kept in stock to accommodate different patients, a large inventory of standard implants is created, and several molds for each type and size of implant may be used. As described below in detail, semi-custom implants provide an intermediate solution between custom-made and off-the-shelf implants. Semi-custom implants reduce the size of inventory and molds required for production, while allowing some degree of patient-specific customization.

Custom or patient-specific implants, when approved by surgeon at 170 for a specific patient, can be manufactured for the patient by rapid prototyping methods, such as stereolithography or other similar methods, or by CNC milling, or other automated or computer-controlled machining, or by robotic methods, at 250. Manufacturing can take place at a manufacturing center or facility in situ or at remote or off-site location. It will be understood that in situ manufacturing is used as a short hand for a manufacturing site of the original equipment manufacturer (OEM), but can be physically located at a different facility of the OEM. Off-site or remote manufacturing will be understood to refer to facilities operated by other manufacturers who are contracted by the OEM for manufacturing all or some of the implants, components or parts for the surgical procedure.

Off-the-shelf implants, when approved by the surgeon a 190, can be manufactured by standard casting methods from bar stock or other stock material at 200, then shaped to a final shape and size by grinding or milling at 210, polished at 220, and then cleaned/passivated at 230. Such off-the-shelf implants can be part of an existing inventory, or mass-produced, or produced by just-in-time agile manufacturing methods.

Semi-custom implants, when approved by the surgeon at 180, can be made from a generic casting at 240, as described below, or by modifying existing standard implant designs to match various features or parameters based on the anatomy of the patient, as described in co-pending patent application entitled Patent-Modified Implant and Associated Method, Ser. No. 12/103,834, filed on Apr. 16, 2008, the disclosure of which is incorporated by reference herein. After the generic casting is modified for certain parameters of a patient, it can be processed at aspects 210-230 to a passivated form. Patient-specific parameters can include parameters relating to the size of the implant, including height, width, various articulation parameters or angles, etc., as discussed in specific example below in reference to FIGS. 3-5.

The surgeon's review of the surgical plan at 140 may further include, at 160, a request for one or more patient-specific alignment guides to be used with the implant. Patient-specific alignment guides are described in co-pending patent applications Ser. No. 11/756,057, filed on May 31, 2007, Ser. No. 11/971,390, filed on Jan. 9, 2008, Ser. No. 12/025,414, filed on Feb. 4, 2008, and Ser. No. 12/039,849 filed on Feb. 29, 2008. The alignment guides can be manufactured at 260 with by rapid prototyping methods, such as stereolithography or other similar methods or by CNC milling, or other automated or computer-controlled machining or robotic methods, and cleaned at 270. The alignment guides, the implants and optionally other disposable instruments (at 272) can be packaged and sterilized at 280, and forwarded to the surgeon or the surgeon's medical facility for implantation at 290.

Figure 1C:
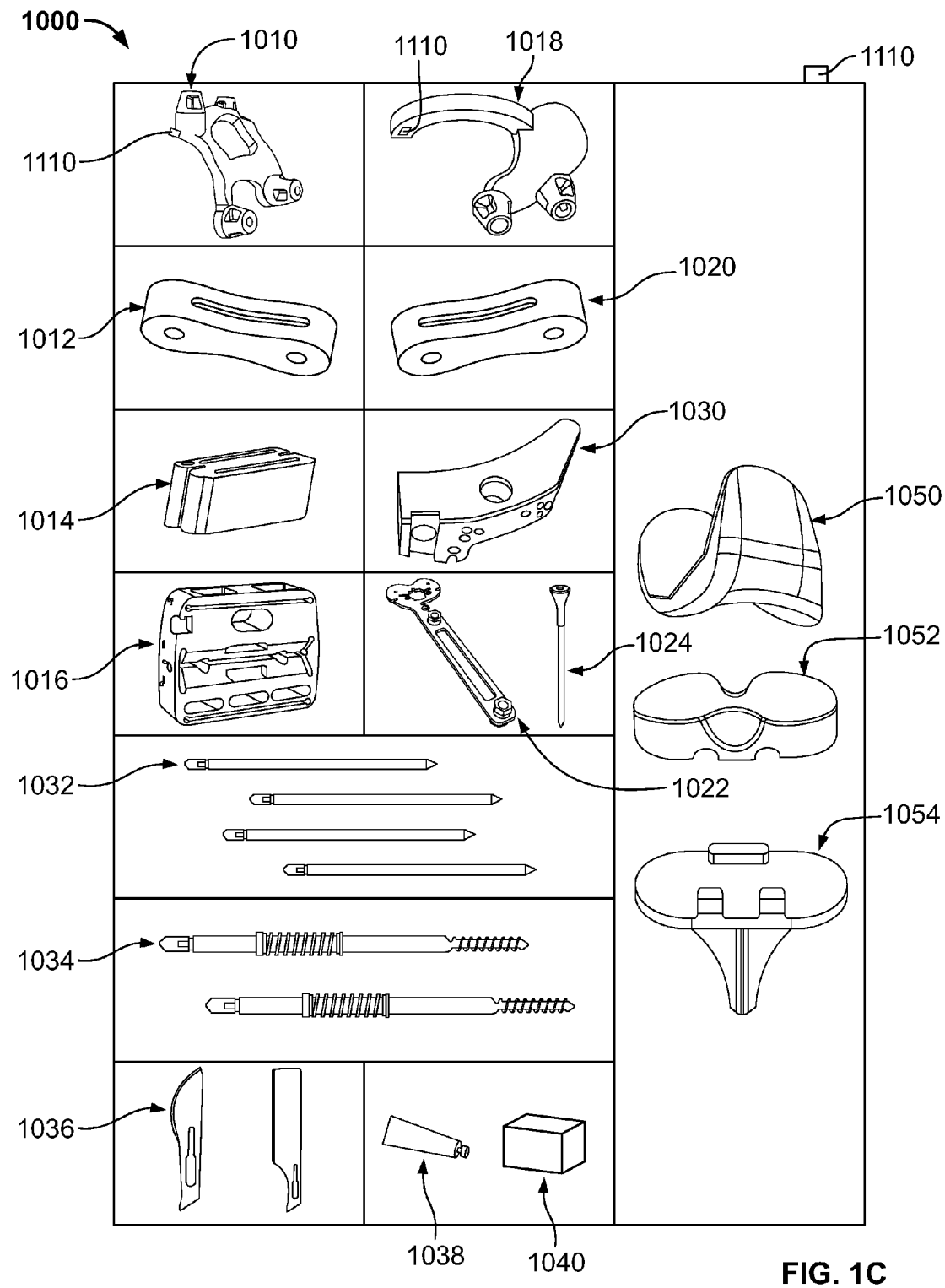
FIG. 1C is a surgical kit according to the present teachings.

The methods described in connection with FIGS. 1A and 1B can be modified to incorporate additional features, as illustrated in FIG. 1C. The additional features can include a preparation of a surgeon kit 1000 at 276 and optionally a tracking procedure in which tracking tags are added at 278 to the various parts that are included in the surgeon kit 1000. The tracking procedure can be incorporated in the manufacturing, cleaning, sterilizing, assembling and boxing the various components up to implantation and can be maintained, for example through the procedures at 260, 270, 230, 272, 274, 276, 280, and 290, as shown in FIG. 1B. The surgeon kit 1000 and can be tracked during assembling/stocking the surgeon kit 1000 with the various components, and the tagged components can be tracked from manufacture to implant procedure.

Referring to FIGS. 1B-1E, a surgeon kit 1000 can be generated at 276. The surgeon kit 1000 can be designed and assembled during the process described above in FIGS. 1A, 1B and 1C and during the manufacturing of the patient-specific alignment guides and implants. The surgeon kit 1000 can be assembled based on surgeon preferences and can include a set of implants, such as, for example, a femoral implant 1050, a bearing 1052 and a tibial implant 1054, for an exemplary knee replacement procedure, or other implant components depending on the surgical procedure and the surgeon's preference. The implants can be patient-specific, of semi-custom or standard off-the-self as described above. In addition to or instead of the implants, surgeon-selected alignment guides (at 160, 165 and 260), other disposable instruments (at 274) and other reusable instrument (at 274) selected according to the surgeon's preferences can be included in the surgical kit 1000. In one embodiment, the surgeon kit can include only instruments, such as, for example, alignment guides and other tools, designed to be disposable.

In the exemplary illustration of FIG. 10, a surgeon kit 1000 for a knee procedure is shown to include a femoral alignment guide 1010, a tibial alignment guide 1018, a femoral drill guide 1012, a tibial drill guide 1020, a femoral distal cutting block 1014, a tibial cutting block 1030, a four-in-one femoral cutting block 1016, a tibial template 1022 with alignment rod 1024. The alignment guides are single-use and disposable. The various drill guides and cutting blocks can be re-sterilazable and reusable, although disposable drill guides, cutting blocks and other tools can also be designed. Additionally, a set of trochar pins 1032 and a set of spring drill pins 1034 can be included. Depending on the surgeon's preferences, various surgical blades 1036 can be added and additional medical products, such as, for example, bone cement 1038, or other medical supplies or biologics 1040.

Figure 1D:
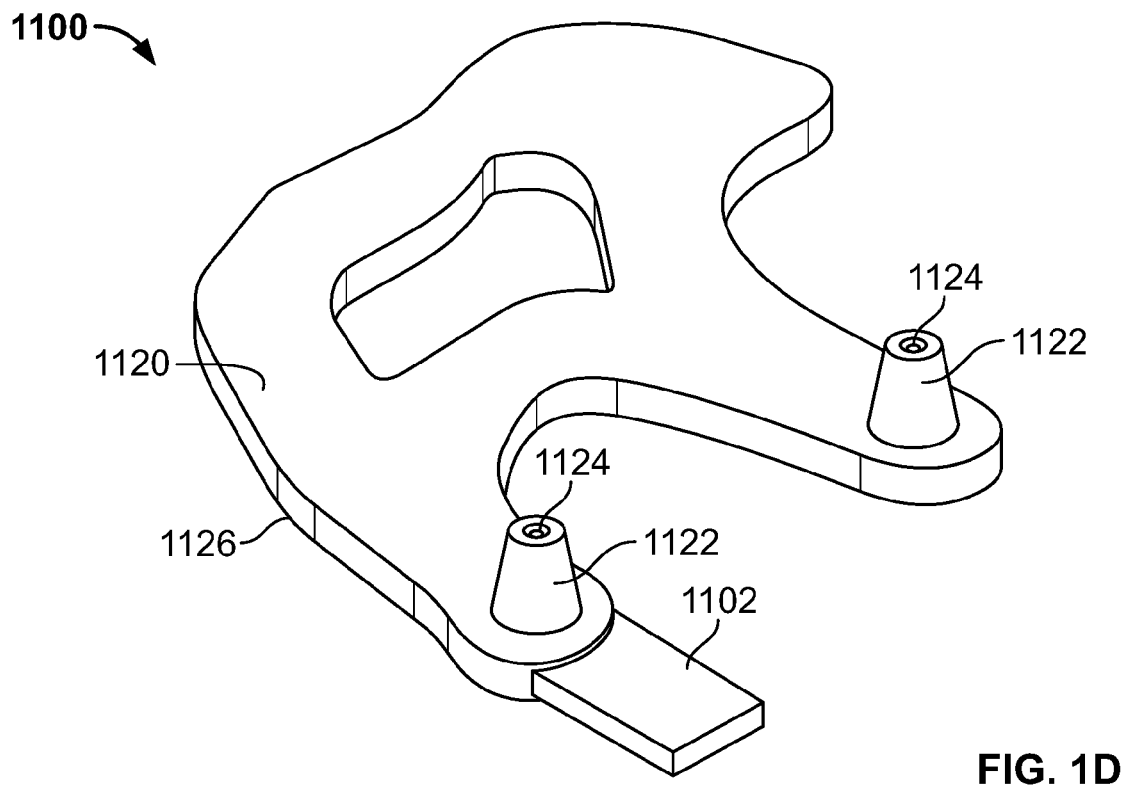
FIG. 1D is a patient-specific alignment guide according to the present teachings.
Figure 1E:
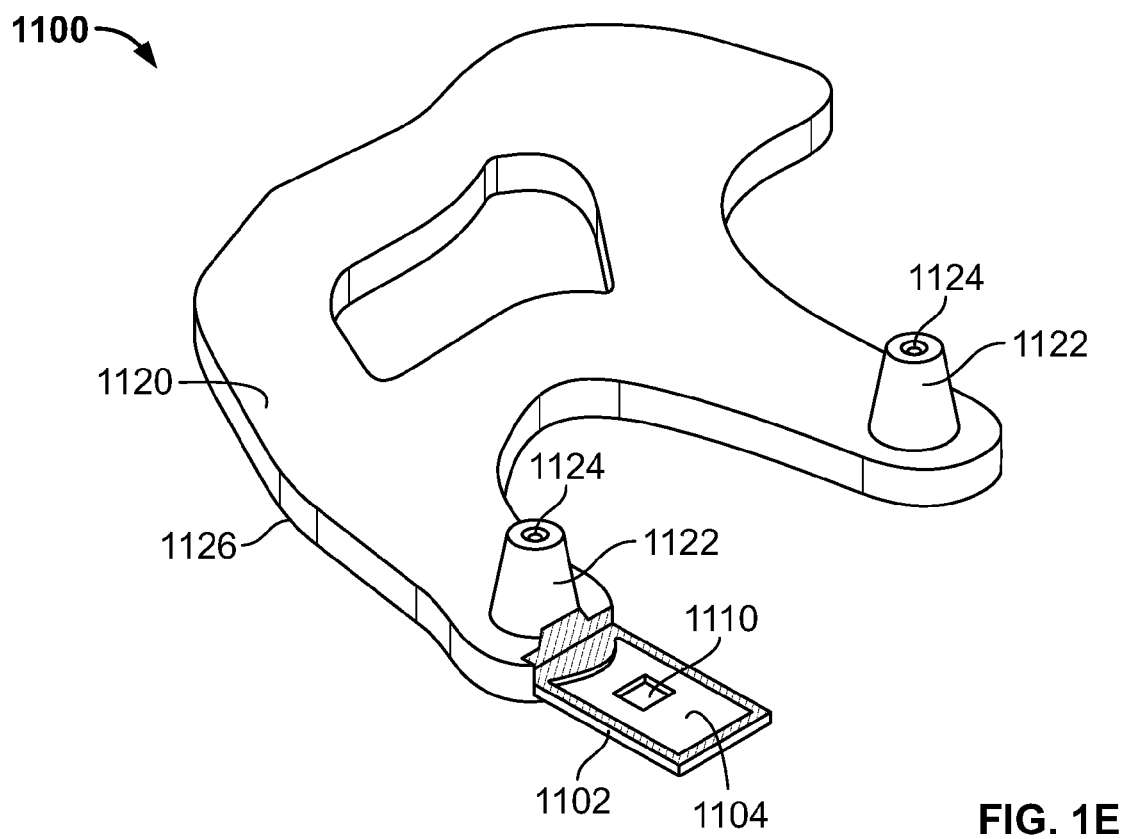
FIG. 1E is a patient-specific alignment guide according to the present teachings.

Referring to FIGS. 1B-1E, a tracking system can be incorporated with the surgeon kit 1000. Tracking tags 1110 can be added at 278 optionally to the alignment guides, the implants and/or the entire surgeon kit 1000. The tracking tags 1110 can be simple barcode tags, or other scan readable tags or radio frequency identification (RFID). The tags 1110 can be added to individual instruments or on the entire surgical kit 1000, outside the box. The tracking tags can include patient-specific information and/or surgeon information, such as, for example, patient's name, age, gender, procedure to be performed, surgeon's name; clinic or hospital location, etc The tracking tags 1110 can be removable. For example, the tracking tags 1110 can be attached with removable glue sticks or frangible attachments. In one embodiment, the tracking tags 1110 can be incorporated in a frangible extension 1102 of an alignment guide 1100, as illustrated in FIGS. 1D-1E. The exemplary alignment guide 1100 can include a body 1120 having a patient-specific engagement surface 1126 for engaging a complementary surface of the corresponding anatomy of the patient and one or more alignment formations 1122 defining guiding bores 1124 for guiding alignment or drill pins or other instruments. The extension 1102 can be prepared or incorporated during the manufacturing process, for example, during the layering process of a rapid prototyping method, and can include a pocket 1104 in which a tracking tag 1110 is inserted, as part of the layering process. Layering can continue and cover the tracking tag 1110. In another embodiment, the extension 1102 can be a blank of larger dimensions from which the pocket 1104 is machined for the tracking tag 1110. The tracking tag 1110 can be removed or broken off by the surgeon. Tracking of the patient-specific (and surgeon) information can be provided for the entire manufacturing procedure from start to finish, i.e., from the manufacturing of the tracked components to assembling the surgeon kit 100 to the implant procedure at the operating theater or site.

Figure 2:
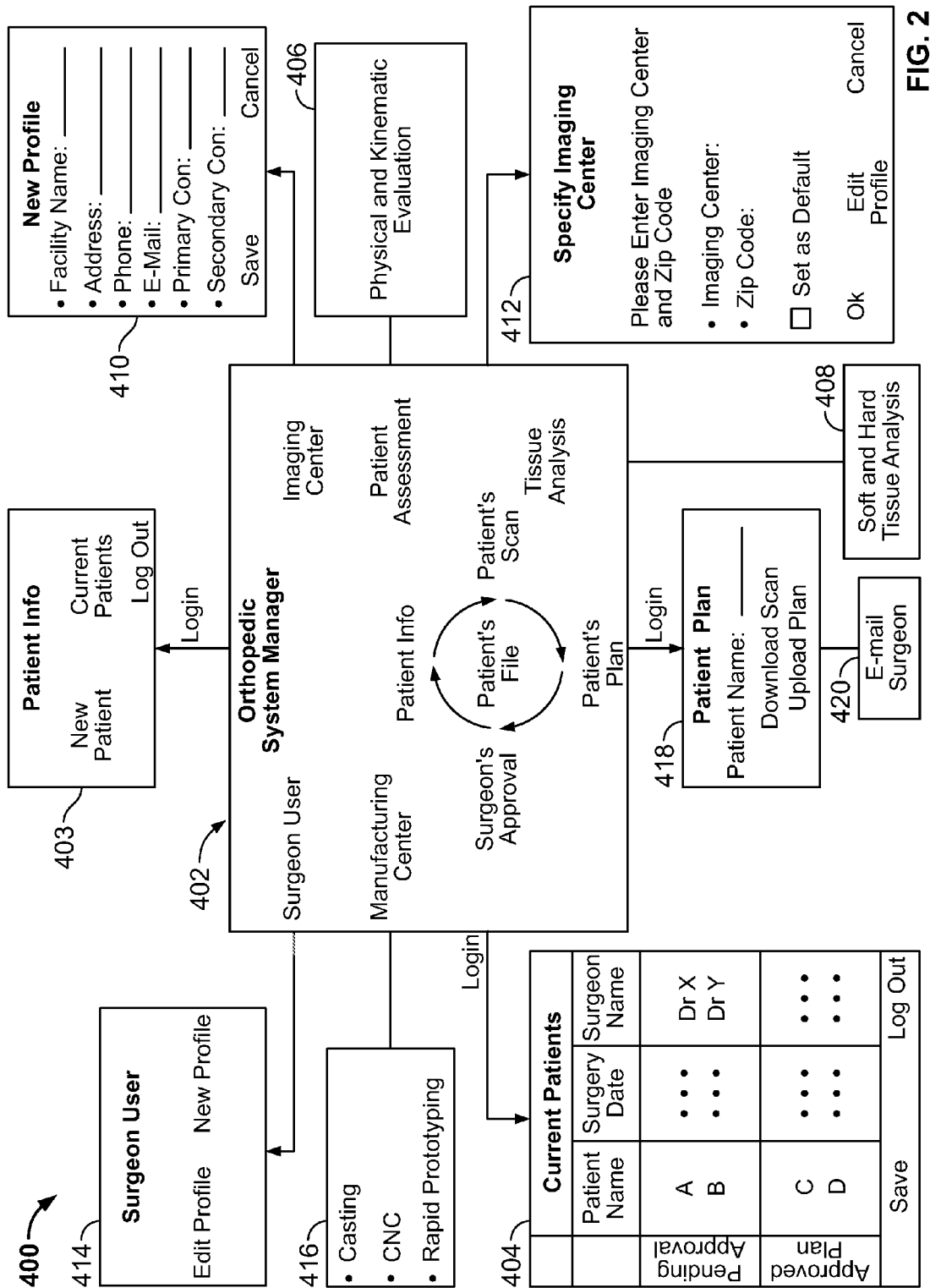
FIG. 2 is a diagram illustrating a computer interface for an implant manufacturing method according to the present teachings.

Referring to FIG. 2, a computer interface 400 to a computer program for the management of the manufacturing method is illustrated diagrammatically. An orthopedic system manager 402 can be in the form of software or other computer program associated with the original equipment manufacturer. The orthopedic system manager 402 can be accessible locally via dedicated computer machines or computer terminal directly communicated with software either by hard wire or wirelessly. The orthopedic system manager 402 can also be accessible remote remotely via the Internet or other remote communication portals using any electronic or other devices that can connect to the Internet or other web-based network, or other similar communication networks, including cable, satellite and telephone-based networks.

The system manager 402 can provide access to patient file information, including lists of all current patients at 403, and surgery dates, surgeons, and approval status of the surgical plan for each patient, at 404. Each patient file can include personal and medical information of the patient, such as, for example, weight, height, gender, age, lifestyle, pertinent medical records and medical history, as well as information on patient assessment that includes physical and kinematic evaluation pertaining to the orthopedic procedure at 406, and soft and hard tissue analysis at 408, including information provided at aspects 120 and 125 of FIG. 1, as discussed above. Imaging center information for patient scans, as discussed in relation to aspects 100 and 110 of FIG. 1, can added or modified at 410, and an imaging center for each specific patient can be specified at 412. Surgeon profiles, including surgeon preferences regarding anatomic axes alignment or implant and instrument preferences that can be taken into account when preparing the preliminary pre-operative plan discussed at aspect 130 of FIG. 1, can be created and edited at 414. Information and selection of manufacturing centers can be accessed at 416 for manufacturing the implants and or alignment guides as discussed in relation to aspects 260, 250, 240, and 210-230 of FIG. 1. The preliminary pre-operative surgical plan for each patient can be provided at 418, as discussed above at 140 in reference to FIG. 1, and e-mailed or otherwise communicated to the patient's surgeon at 420.

Figure 3:
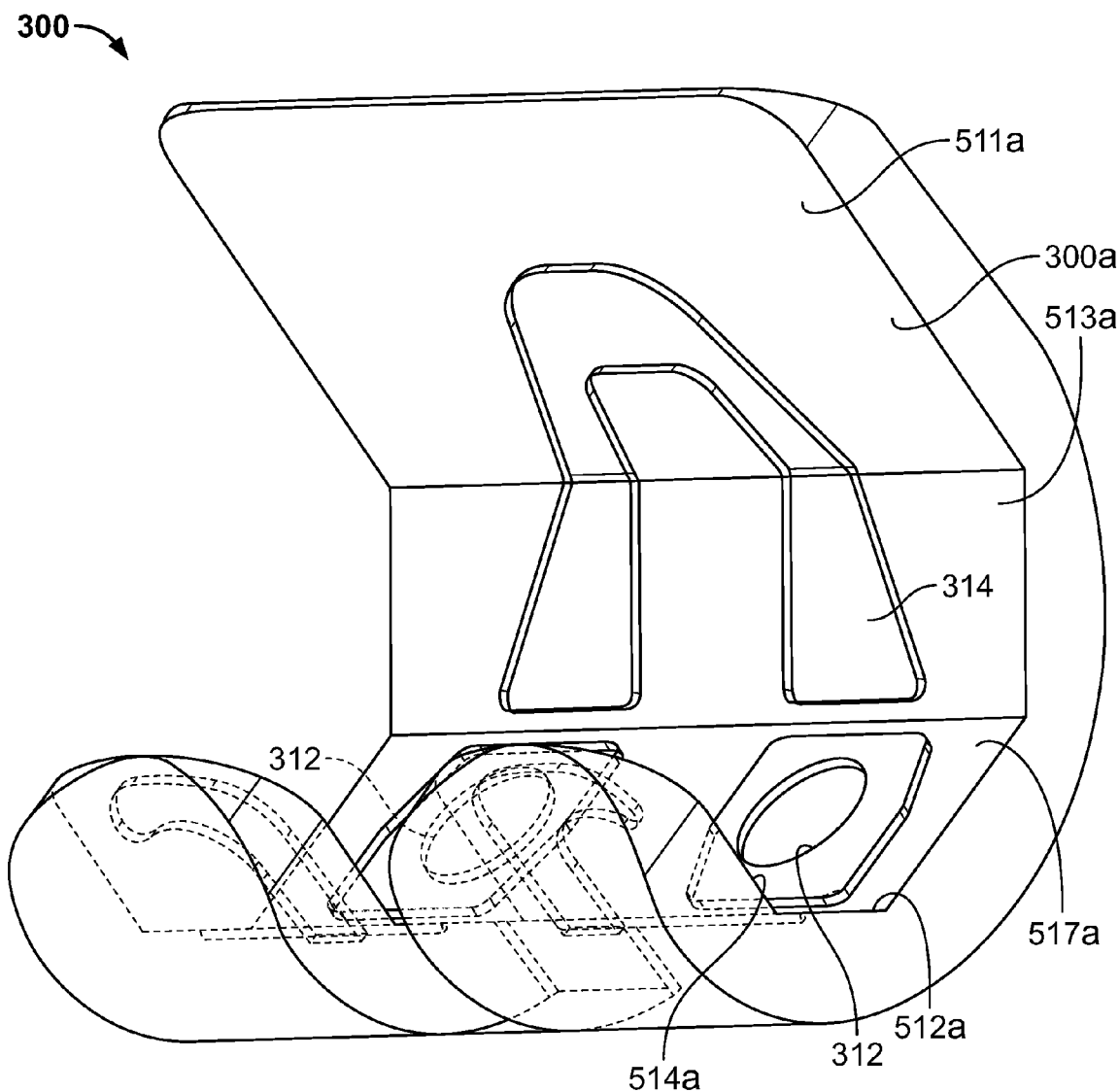
FIG. 3 is perspective view of a generic casting of an implant according to the present teachings.
Figure 4:
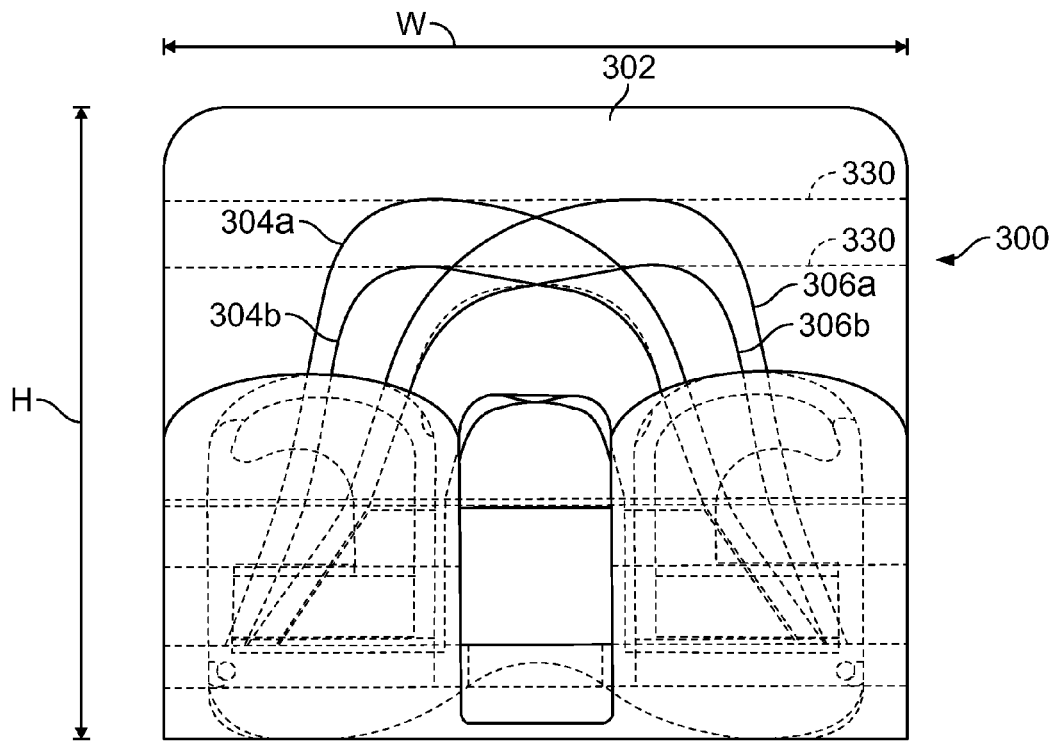
FIG. 4 is a posterior view of a generic casting according to the present teachings.
Figure 4A:
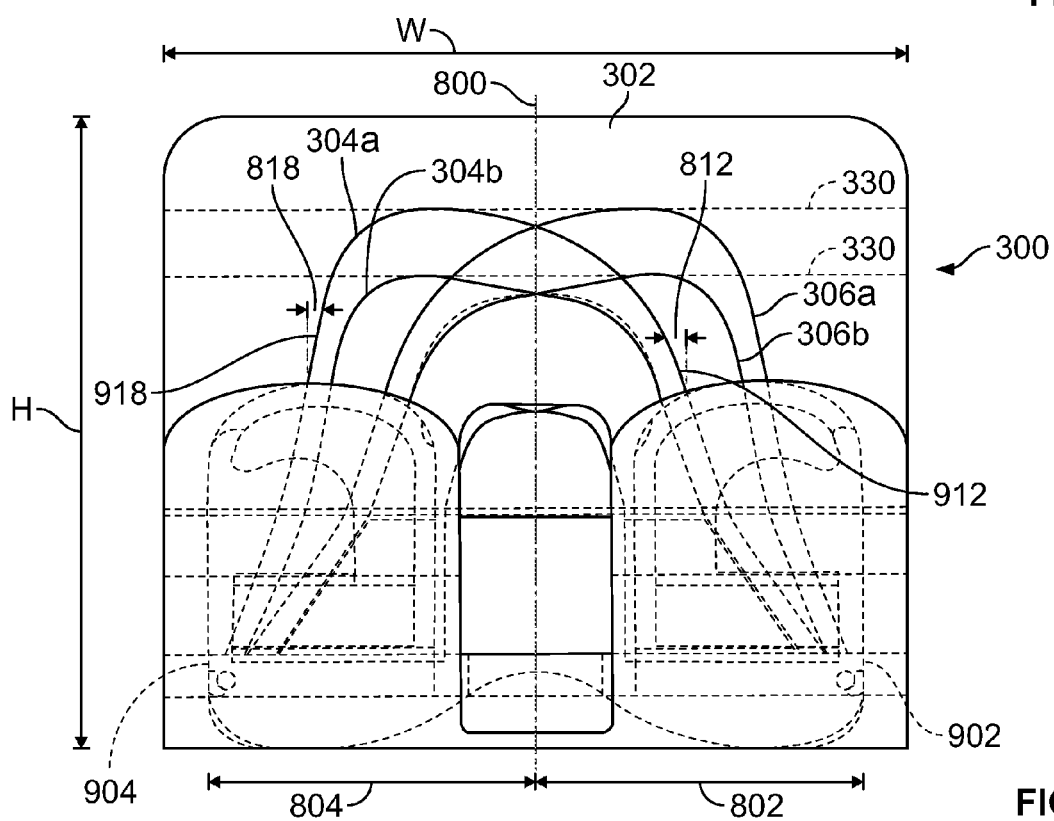
FIG. 4A is a posterior view of a generic casting including a plurality of additional modifiable features according to the present teachings.
Figure 5:
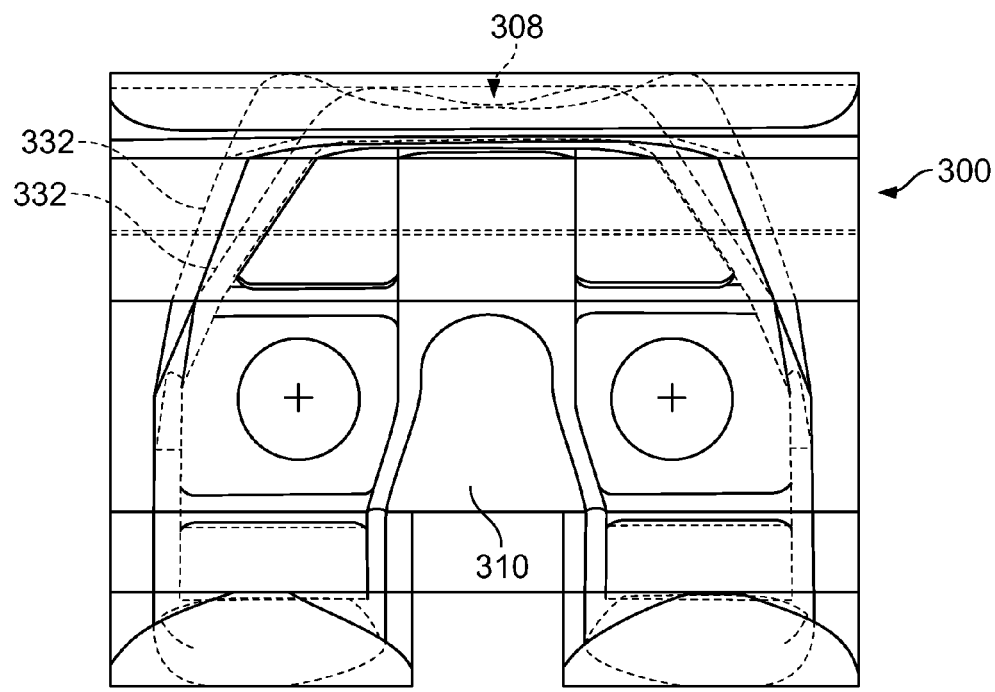
FIG. 5 is a plan view of a generic casting according to the present teachings.
Figure 5A:
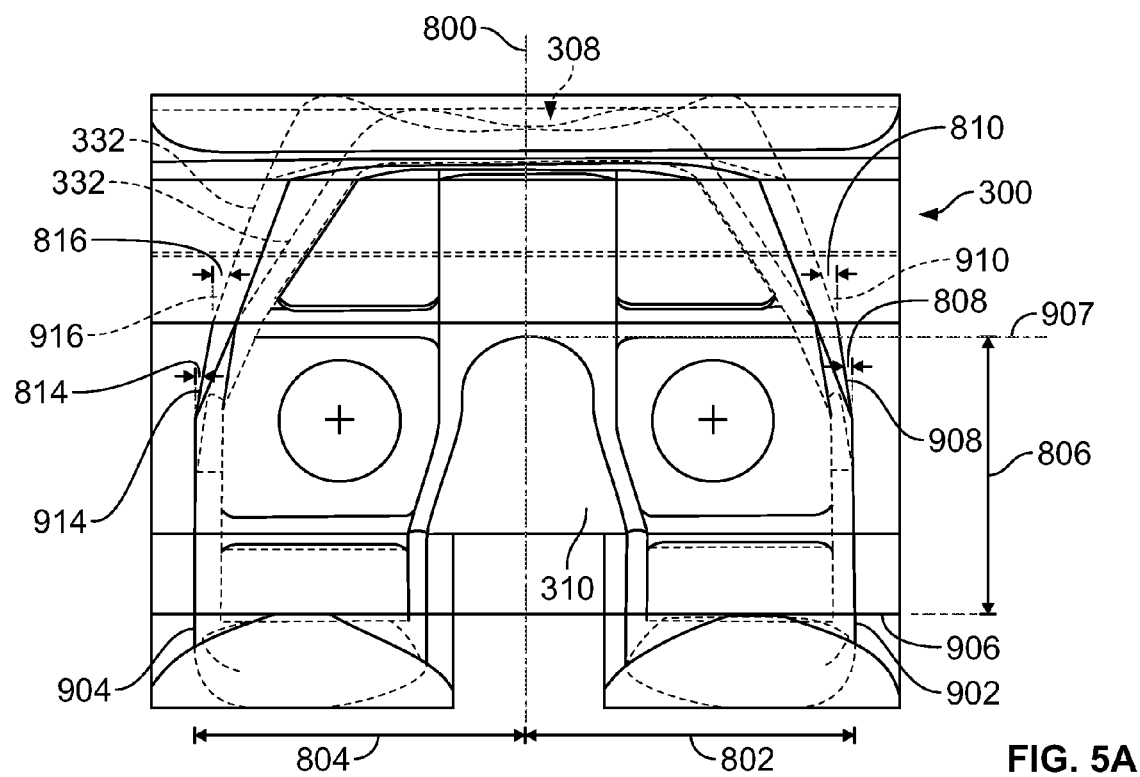
FIG. 5A is a plan view of a generic casting including a plurality of additional modifiable features according to the present teachings.

As discussed above at aspects 150 to 190 of FIG. 1, one implant option includes manufacturing semi-custom implants by generic casting. Illustrative examples of generic casting of a semi-custom femoral implant/component are shown in FIGS. 3-5. A generic casting 300 of the implant is a casting that is more specialized than ordinary bar stock, from which any size of implant can be made, but less specialized than the off-the-shelf implants that are available in a particular number of sizes, typically six-to ten sizes and are finished from specific castings of those sizes. The generic casting can be made in a size and shape that can accommodate a range of variable features for the implant, and at the same time can be machined to multiple sizes, such as three or four smaller sizes. In contrast, off-the-shelf implants require a mold or casting for each offered size, and a larger inventory of available sizes for each implant component. The generic casting can generally include geometric features which are size/shape and/or patient-independent or universal, and also features that are size/shape or patient-specific, as discussed in the examples below. More particularly, the generic casting can include at least one geometric feature that will remain unchanged for any patient or universal feature, and at least one geometric feature that can be specifically customized for and is specific to a particular patient. Additionally, generic castings can be provided in the same sizes as off-the-shelf components, although generic castings can have different shapes than off-the-shelf components.

Referring to FIGS. 4 and 5, an exemplary generic casting 300 of a femoral implant is illustrated. In this example, the generic casting 300 can have an anterior flange 302 of medial-lateral width W, and/or a height H and/or other geometric dimensions to accommodate multiple sizes of femoral implants. For example, multiple sizes of left-sided implants 304a, 304b, and various sizes of right-sided implants 306a, 306b can be formed by a single generic casting. In addition to multiple sizes, multiple shapes can be made from a single generic casting. Appropriate markings or indentations or score lines for cutting to size can be provided, such as height markings 330, for example. The implant for a particular patient can be formed from the generic casting 300 by selecting particular features, such as the width W or height H, or other geometric features for a particular patient and machining the generic casting 300 to provide the size, dimension or shape, or combinations thereof for that particular geometric feature.

Referring to FIG. 5, the generic casting 300 does not include a patella track feature, but provides an area in which a custom patella track 308 can be machined at a custom angle or custom shape for each specific patient. The generic casting 300 can also include additional material in the intercondylar notch area 310 to allow for custom machining of the intercondylar notch area 310 to accommodate various types of articulation or constraint in relation to a tibial implant, such cams or intercondylar boxes, and other contact areas for articulation with the tibial implant in accordance with a kinematic plan for the joint of the specific patient. Custom shapes of various other portions of the implants can also be prepared fro the generic castings. Separate molds for posterior stabilized and cruciate retaining articulations can be made, each mold capable of accommodating multiple sizes of the corresponding implant type. For example, the intercondylar notch area 310 can be machined for line or area contact with the articular surfaces of a tibial implant of various degrees of flexion. Exemplary articulations are disclosed in commonly assigned U.S. Pat. No. 6,589,283, U.S. Pat. No. 6,413,279, and U.S. Pat. No. 6,165,223, and in co-pending U.S. patent application Ser. No. 10/840,765 filed on May 6, 2004, all of which are incorporated herein by reference. Various markings 332 corresponding to different sizes can be provided.

Referring to FIG. 3, the generic casting 300 can include at least one patient-independent or universal feature, such as, for example, universal cement wells 312 or other universal features. Such universal features can be used with any internal geometry 314, which can be machined into the generic casting 300 to accommodate the appropriate shape and/or size for a specific patient.

Figure 5B:
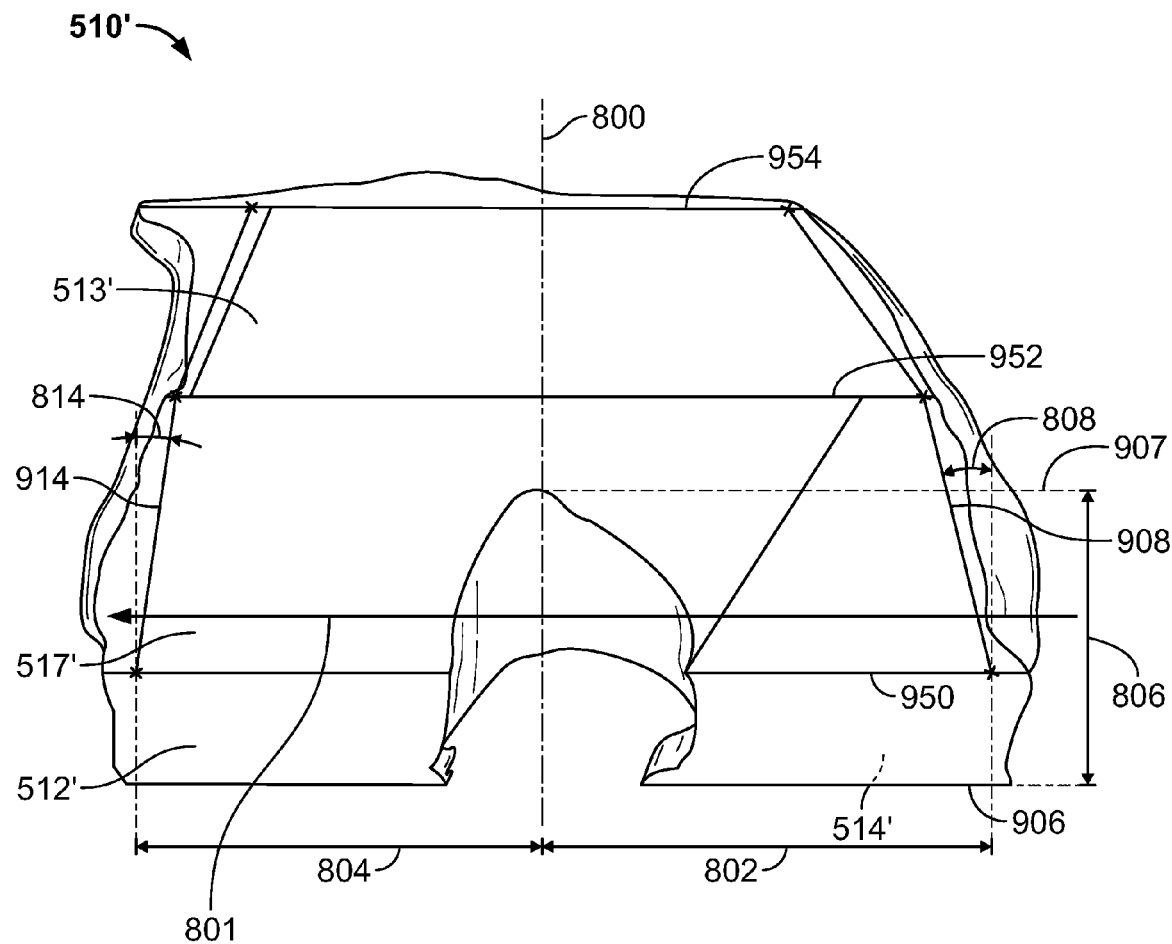
FIG. 5B is a distal view of a three-dimensional image of the patient's distal femur showing planned resection planes according to the present teachings.
Figure 5C:
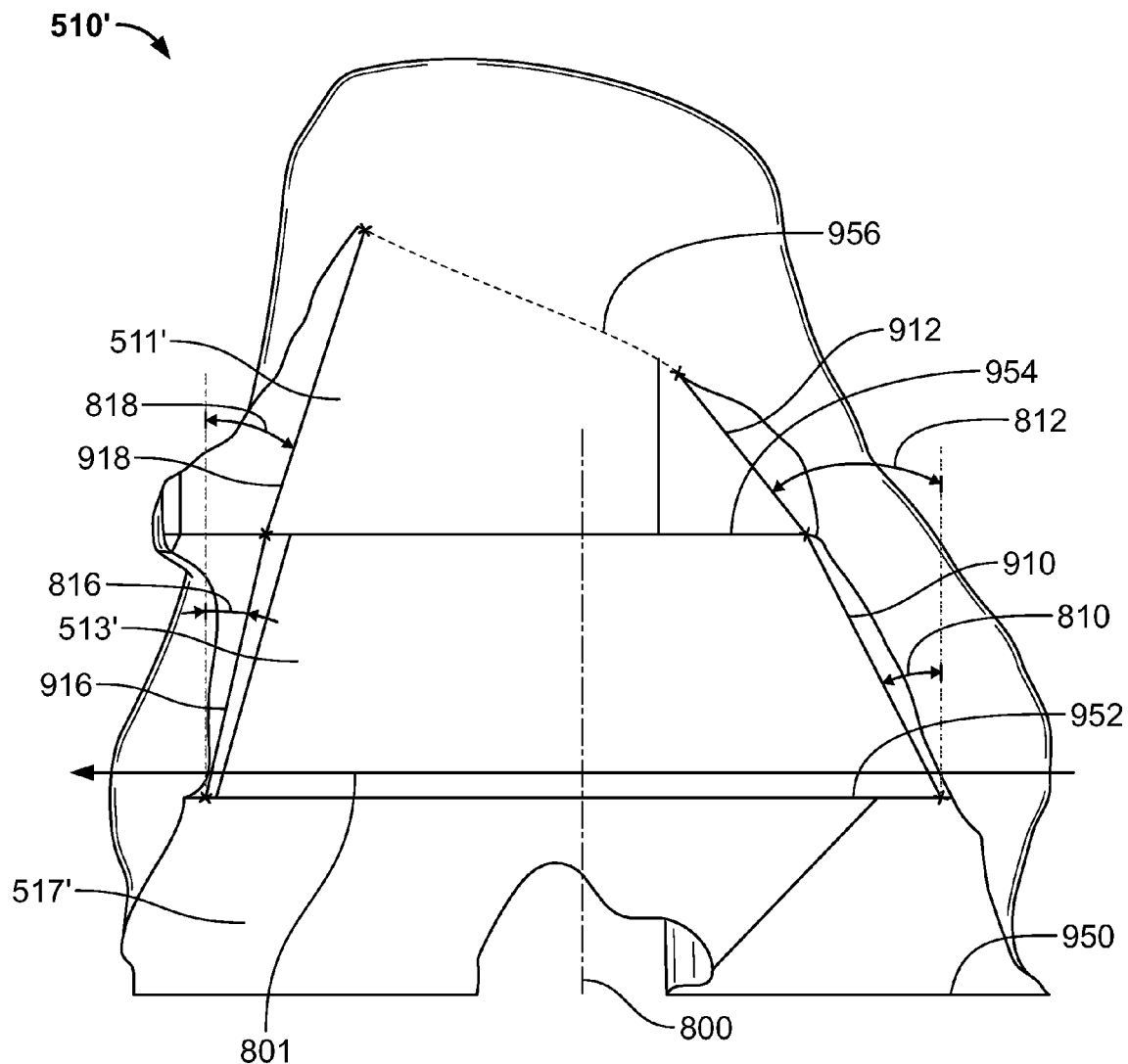
FIG. 5C is a anterior view of a three-dimensional image of the patient's distal femur showing planned resection planes according to the present teachings.

Referring to FIGS. 3, 4A, 5A, 5B and 5C, a semi-custom implant (304a, 304b, 306a, 306b) can also be generated from a generic casting 300 by customizing a plurality of features based on the patient's anatomy during the pre-operative planning stage in addition to or instead of the parameters discussed above. The generic casting 300 can include a standard, non-custom articulation surfaces for the medial and lateral condyles and an internal bone engagement surface 300a for engaging the resected femur and including five internal planes 511a, 513a, 517a, 512a and 514a (FIG. 3) corresponding to anterior cut plane 511', anterior chamfer plane 513', distal cut plane 517', posterior chamfer plane 512' and posterior cut plane 514' (FIGS. 5B and 5C). The internal bone engagement surface 300a and corresponding internal planes of the generic casting 300 can correspond to standard, i.e., non-custom, sizes for the femoral implant. By selecting a relatively large number of parameters corresponding to the patient's anatomy, as captured in the three-dimensional image of the corresponding joint portion of the patient, the semi-custom implant can be made to correspond to the patient's anatomy as closely as desired while retaining the internal geometry corresponding to the resection planes in the sagittal view. More specifically, in an exemplary embodiment, at least nine parameters of the implant can be patient-specific, including three lengths and six angles, as discussed below in reference to the preoperative plan for the specific patient and the various planned resection planes.

In an exemplary embodiment of the preoperative plan, an image of the patient's anatomy, i.e. the distal femur 510' of the patient indicating the planned cut planes is illustrated in FIGS. 5B and 5C. FIG. 5B represents a distal view of the three-dimensional image of the distal femur 510', as reconstructed by MRI, CT or other scans. The planned resections indicated on the image include medial and lateral sides of a posterior chamfer plane 512', of a distal cut plane 517', and of an anterior chamfer plane 513'. The most anterior point of the intercondylar notch is indicated by a tangent line at 907. FIG. 5C represents an anterior view of the three-dimensional image of the distal femur 510', and illustrates the distal cut plane 517', anterior chamfer plane 513', and an anterior cut plane 511'. The straight edges of the various cut planes are indicated as follows in reference to FIG. 5C: posterior distal edge 950 is the posterior edge of the distal cut plane 517'; anterior distal edge 952 is the anterior edge of distal cut plane 517'; distal anterior edge 954 is the distal edge of the anterior cut plane 511'; and proximal anterior edge 956 is the proximal edge of the anterior cut plane 511'. FIG. 5B also illustrates the posterior distal edge 950, the anterior distal edge 952, and the distal anterior edge 954.

A representative, but not exhaustive list of patient-specific parameters that can be selected at the preoperative stage for incorporation into the implant design after a particular size implant has been selected is indicated in FIGS. 4A and 5A-C.

Specifically, a central plane 800 perpendicular to the epicondylar axis 801 of the distal femur 510' can be identified through the center of and orthogonal to the medial-lateral width W of the generic casting 300. The central plane 800 can be used as a reference plane for the bone cuts and the various patient-specific parameters to be used in modeling the semi-custom implant. The specified parameters can include, for example, three distances/lengths of the implant and six angles of the implant, each of which can be modified pre-operatively to be patient-specific such that they correspond to conform to the particular patient's anatomy. It will be appreciated that a lesser or greater number of parameters or different parameters can be use to customize and optimize the implant for the patient. The following exemplary parameters are illustrated in FIGS. 4A and 5A-C: medial condyle width 802, lateral condyle width 804, notch height 806, first, second and third medial angles 808, 810, 812; and first, second and third lateral angles 814, 816, 818.

In particular, and referring to FIGS. 5B and 5C, the medial condyle width 802 is defined as the distance between the central plane 800 and the farthest medial point/tangent line 902 (but not part of an osteophyte) on the posterior distal edge 950. The lateral condyle width 804 is defined as distance between the central plane 800 and the farthest lateral point/tangent 904 on the posterior distal edge 950 (but not part of an osteophyte). The notch height 806 defined as the distance along the central plane 800 from the posterior cut plane 514' at edge 906 to the most anterior point/tangent line 907 on the notch (but not part of an osteophyte). The first medial angle 808 is defined as the angle between the central plane 800 and the line 908 connecting the medial-most points on the posterior distal edge 950 and the anterior distal edge 952. The second medial angle 810 is defined as the angle between the central plane 800 and the line 910 connecting the medial-most points on the anterior distal edge 952 and the distal anterior edge 954. The third medial angle 812 is defined as the angle between the central plane 800 and the line 912 connecting the medial-most points on the distal anterior edge 954 and the proximal anterior edge 956. The first lateral angle 814 is defined as the angle between the central plane 800 and the line 914 connecting the lateral-most points on the posterior distal edge 950 and the anterior distal edge 952. The second lateral angle 816 is defined as the angle between the central plane 800 and the line 916 connecting the lateral-most points on the anterior distal edge 952 and the distal anterior edge 954. The third lateral angle 818 defined as the angle between the central plane 800 and the line 918 connecting the lateral-most points on the distal anterior edge 954 and the proximal anterior edge 956.

Referring to FIG. 1A, when the above parameters 800, 802, 804, 806, 808, 810, 812, 814, 816, 818 are identified in the pre-operative planning stage, an image of a semi custom implant customized with these parameters can be displayed at 135 for review and comparison with the image of the patient's anatomy. The values of the parameters 800, 802, 804, 806, 808, 810, 812, 814, 816, 818 can be adjusted, as desired, and the implant with the adjusted or finalized parameters can selected at 137 and forwarded to the surgeon for review at 140 together with the preoperative plan which includes surgeon's preferences of implants, guides and other instruments, as described above in connection with FIG. 1. The preoperative planning procedure can proceed as discussed above.

As discussed above, each semi-custom implant has an internal bone engagement geometry including five planes 511a, 513a, 517a, 512a and 514a corresponding to the resection planes and at least nine patient-specific parameters, including the three lengths and six angles described above.

It will be appreciated from the above discussion that generic casting can greatly reduce inventory, machining costs and investment in mold tooling, while at the same time accommodating sizes and geometric features specific to a patient. Specifically, each implant type can be formed from a generic casting that can accommodate multiple AP sizes corresponding to medial-lateral widths, such as four sizes, for example. For implants that are available in eight sizes, generic casting can reduce inventory by a half, using two molds total for eight sizes. Further, additional reductions in inventory can be obtained by combining right and left side implants into a single generic casting, as discussed above in relation to FIG. 4. Thus, generic castings reduce side-specific castings and also allow for various custom shapes and features.

Figure 13A:
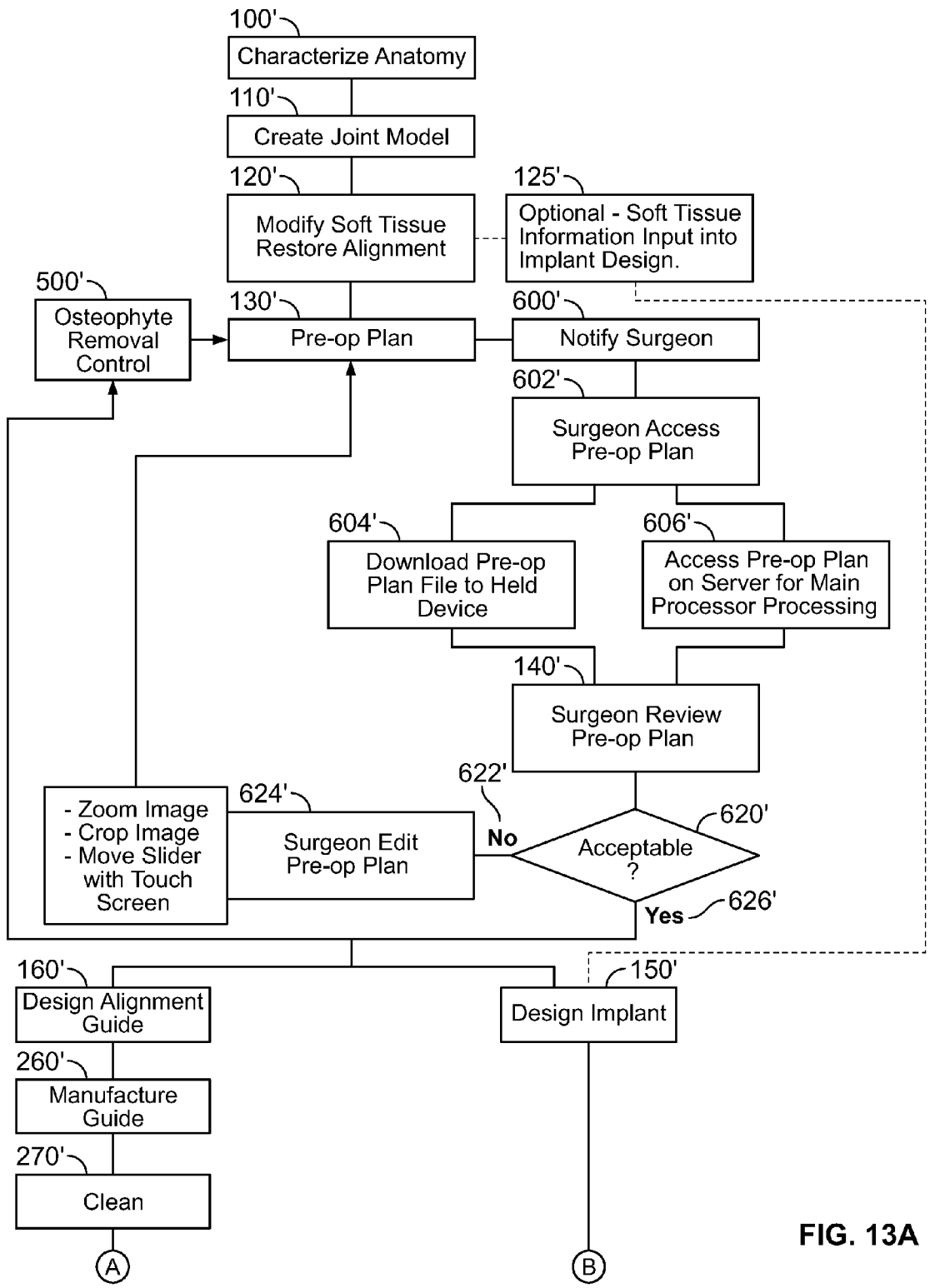
FIGS. 13A and 13B illustrate a flowchart of a method of implant and guide design.
Figure 13B:
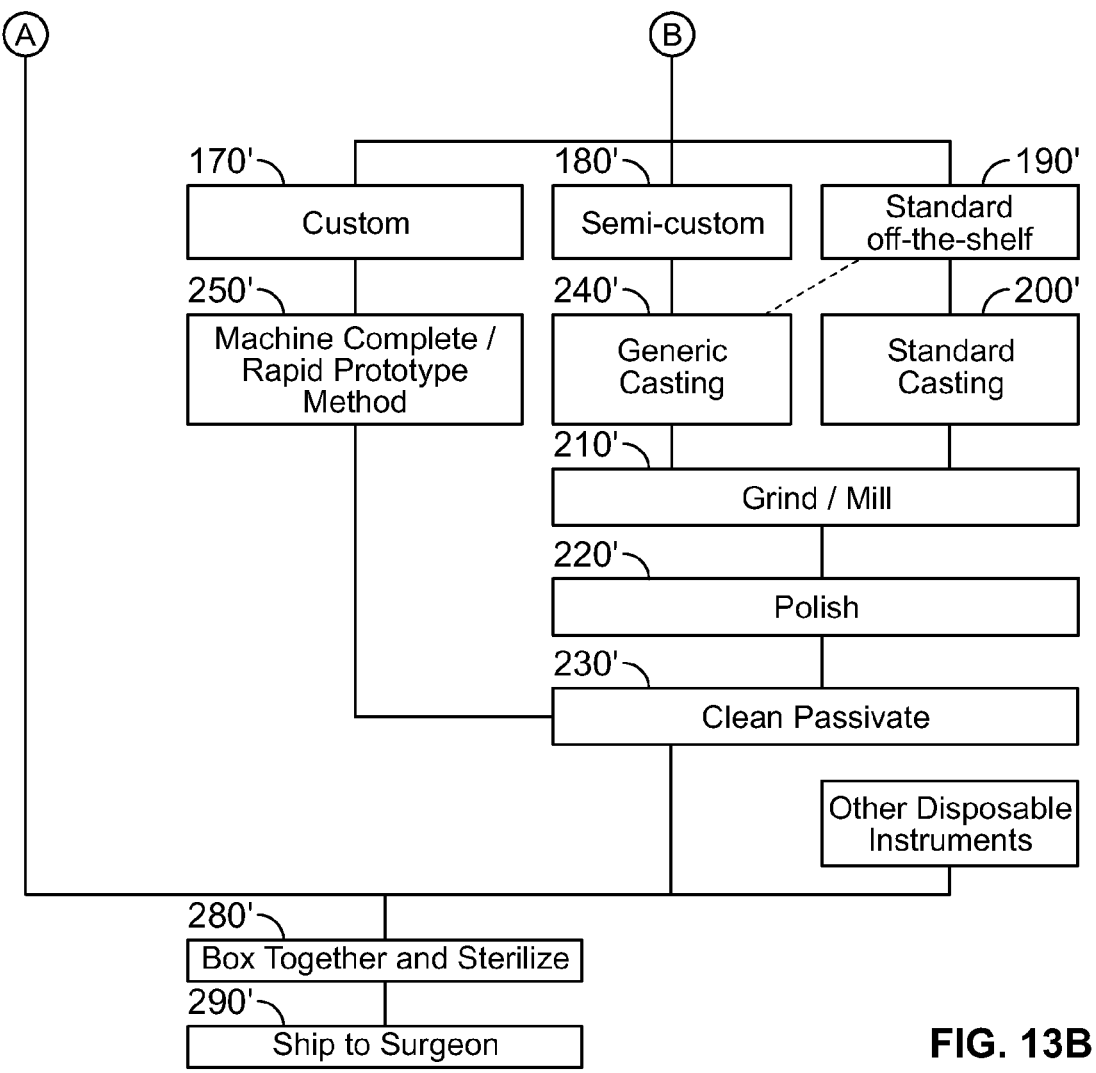

The process can then be followed as illustrated in FIGS. 13A and 13B as discussed above in relation to FIG. 1. The blocks in FIGS. 13A and 13B that are illustrated with the same reference numerals as in FIG. 1, but augmented with a prime are not discussed in further detail, but are discussed above in FIG. 1 and include substantially similar processes. In addition to the various applications discussed above, input from a surgeon or other appropriate user can be provided with a handheld device, as discussed above. As illustrated in FIGS. 13A and B, a handheld device can be used by the surgeon to review the pre-operative plan at 140'. It will be understood, however, that the process for providing a selected implant and tools can be similar to that discussed above, for example, with reference to FIG. 1

Figure 14:
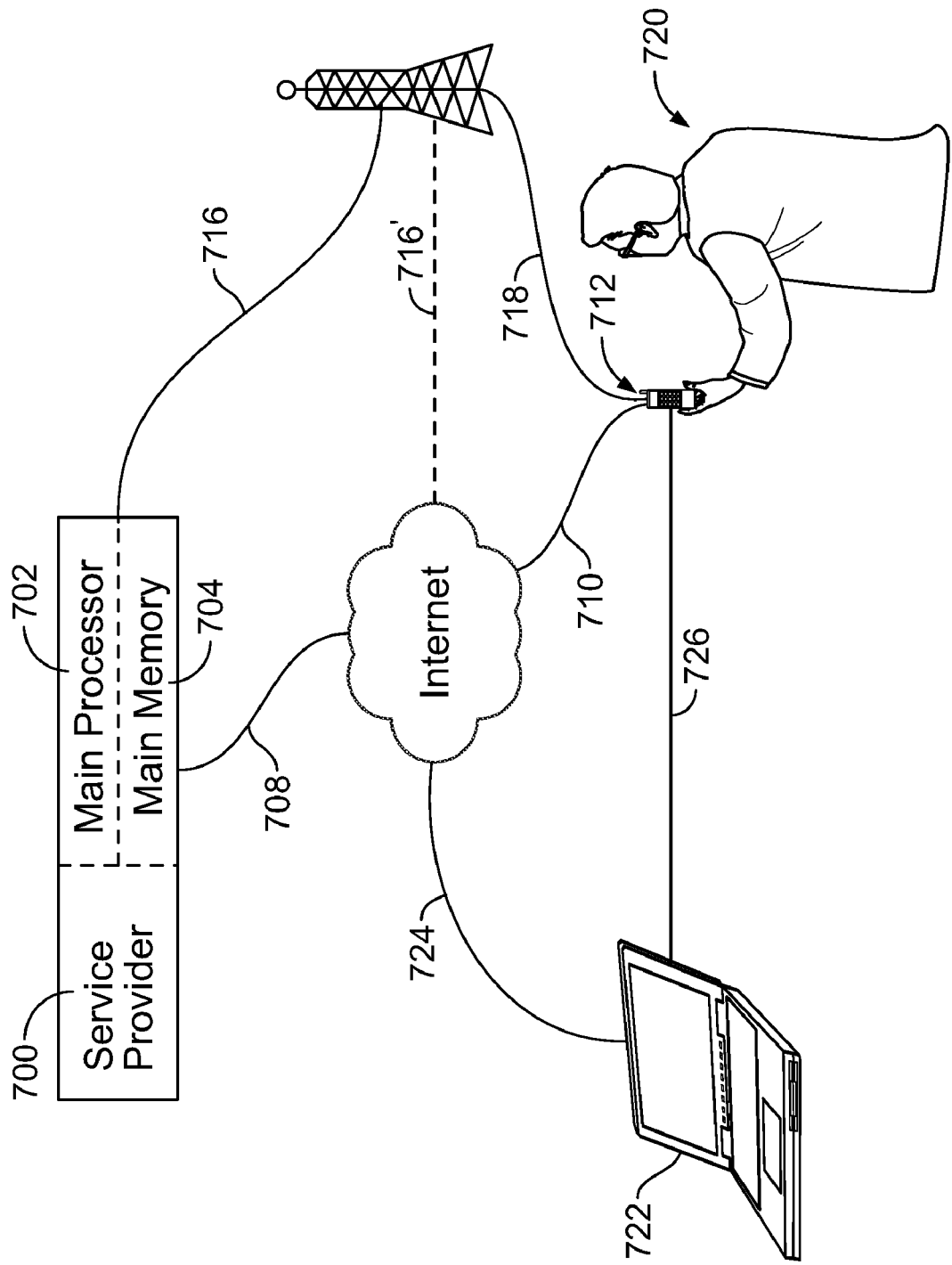
FIG. 14 is a schematic view of hardware and a user.

With reference to FIG. 14, a schematic diagram illustrating main or exemplary hardware components for the process illustrated in FIGS. 13A and 13B is illustrated. The pre-operative plan or preliminary pre-operative plan from block 130 and 130' can be developed or produced by a service provider 700. The service provider 700 can own, operate, manage, or the like a main processor 702 and a main memory 704. The main processor and main memory 702, 704 can be at the service provider 700, in communication with the service provider 700, or otherwise controlled, maintained, or used by the service provider 700. Further, the main processor and main memory 702, 704 can be incorporated into a single server system. Regardless, the main processor 702 can process or execute a program, such as a program to develop the pre-operative plan, accept inputs from the surgeon, and augment or generate the final pre-operative plan. In addition, the main processor 702 can also be used to design and output the implant and alignment guide in blocks 150, 150', and 160, 160'.

As discussed above, and further herein, the pre-operative plan can be delivered or accessed by the surgeon via notification or surgeon access in block 600', 602'. The access or delivery of the pre-op plan can be via an internet or worldwide web connection 706 that uses a first communication method 708 from the service provider 700 and a second communication method 710 to a handheld device 712. It will be understood that the first and second communication method 708, 710 can be wired or wireless and can both be the same. Alternatively, or in addition to an internet connection a cell or mobile phone connection system 714, such as a tower, cell phone, antenna, can be provided. A first communication line 716 can transmit a communication through the mobile phone connection system 714. It will be understood that the service provider can communicate directly with the mobile phone connection system 714 via connection 716 or through an indirect connection 716', such as an internet connection. A second communication line 718 can be used by a surgeon 720 with the handheld device 712. Again, it will be understood, that the first and second communication system 716, 716', and 718 can be wired or wireless and can be the same or different. In addition, an intermediate system, such as a laptop or desktop computer 722 can be in communication with a system, such as the internet 706 via a first communication system 724 and the handheld device 712 can be interconnected with the computer 722 via a second communication system 726. Again, the first and second communication system 724, 726 can be the same or different and be wired or wireless.

With further reference to FIGS. 13A, 13B, and 14, the pre-operative plan from block 130' can be delivered to a surgeon or accessed by a surgeon in any appropriate manner, such as via the internet 706 or cell communication 714. The pre-operative plan can be the preliminary pre-operative plan as discussed above. The pre-operative plan can include or be saved as a data file, in the main memory 704 associated with the main processor 702 of the service provider 700, of an appropriate type including image data, patient data, resection area data, etc. The pre-operative plan can be generated and stored by the service provider 700. The service provider 700 can be any appropriate service, such as an implant and/or guide manufacturer or specification producer. A specification producer can be a service that provides specifications for an implant or guide to a manufacturer for production.

The service provider 700 can notify the surgeon 720 or user that the preliminary pre-operative plan is ready for review in block 600'. The notification that the pre-operative plan is prepared can be performed in any appropriate manner. For example, an electronic mail notification can be sent to the surgeon 720, a text message can be sent to the surgeon 720, a telephone call can be made to the surgeon 720 via landline or a wireless connection, as illustrated in FIG. 14. Regardless, the surgeon can be notified that the pre-operative plan is ready for review in block 600 through the use of the mobile device 712.

Once the surgeon 720 is notified that the pre-operative plan is ready for review, the surgeon 720 can access the pre-operative plan in block 602'. The surgeon can access the pre-operative plan in one or a plurality of ways in block 140'. For example, the surgeon 720 can download the pre-operative plan to the handheld device in block 604'. Alternatively, or in addition thereto, the surgeon 720 can access the main processor/memory 702, 704 to review the pre-operative plan in the main memory 704 in block 606' with the handheld device 712. It will be further understood that the surgeon 720 may also access the plan with the computer or terminal 722 by downloading the pre-operative plan data file to the computer 722 on which appropriate software is installed to access the pre-operative plan. The surgeon 720 may also view a printout of the pre-operative plan for manipulating or commenting on the pre-operative plan, or any other appropriate manner.

If the surgeon 720 downloads the file to the handheld device 712, the file can be downloaded to the handheld device 712 using any appropriate transfer protocol or communication system, as illustrated in FIG. 14. For example, the handheld device 712 can be connected to the computer 722 through an appropriate communications cable or protocol 726, such as Bluetooth®, a wireless communication protocol or a Universal Serial Bus (USB) cable. Once the file is downloaded to the handheld device 712, a program on the handheld device 712 can execute or read the file and display images for the surgeon 720. The surgeon 720 can then review the plan in block 140'. For example, as illustrated in FIG. 7, a view of a bone to be resected can be displayed along with the slider bars 520 for allowing editing or augmentation of the pre-operative plan by the surgeon.

Figure 15:
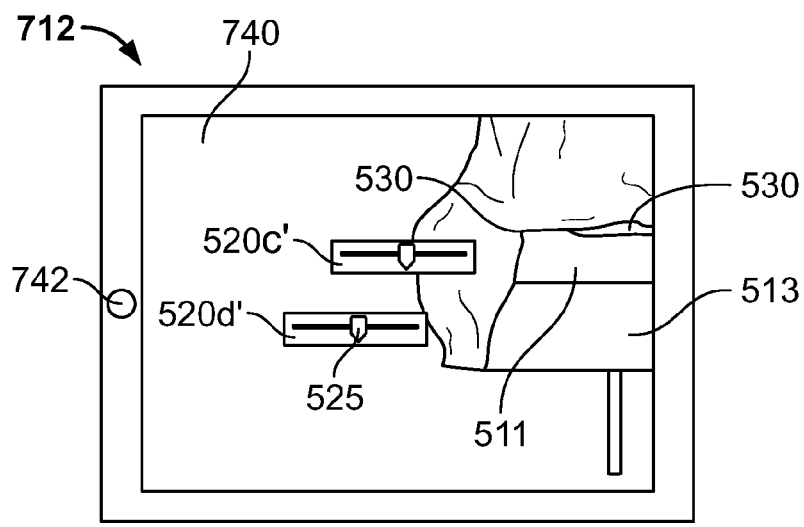
FIG. 15 is a plan view of a display of a device.

The view of the images, including the slider bars 520, can be augmented for the handheld device 712. For example, a cropped and zoomed image may only include a portion of the bone or region to be cut or resected for viewing by the surgeon. For example, as illustrated in FIG. 15, the handheld device 712 can include a view screen 740 that displays an image of the bone to be resected, but only includes a portion thereof, such as a lateral portion of a distal femur. The zoomed and cropped image can include fewer than all of the slide bars 520, such as only the slide bars 520'c and 520'd. The slide bars 520'c and 520'd can be illustrated and accessed by the surgeon to change data in the file for creation of appropriate instruments and implants for the specific patient or for augmentation of semi-custom or selection of an off-the-shelf instrument and implant.

The surgeon 720 can access or change the pre-operative plan file using the slide bars 520'c and 520'd through any appropriate access or manipulation process. For example, the screen 740 of the handheld device 712 can be a touch screen. Accordingly, the surgeon 720 can touch the screen with a finger or stylus to move the slider or marker portion 525 on the slider bars 520'c and 520'd. Alternatively, or in addition thereto, a trackball or other pointer device 742 can be provided to access and move the slider bars 520'c and 520'd. It will be understood that the handheld device 712 can have any appropriate input devices, such as an external or connected input devices, that can be mapped for appropriate command inputs into the system for augmenting the pre-operative plan file. The changes, if made by the surgeon, can then be saved to the pre-operative plan file to generate an edited pre-operative plan file.

If the surgeon 720, after review of the pre-operative plan in block 140', finds the plan to be unacceptable in block 620', the NO path 622' can be followed for the surgeon 720 to edit the plan in block 624'. The surgeon 720 can edit the plan in block 624 in any appropriate manner, such as by moving the slider bars 520'c and 520'd, or any other appropriate slider bars. Alternatively, the surgeon 720 can edit the pre-operative plan in any appropriate manner, including those discussed above. Moreover, the surgeon 720 can input changes into the pre-operative plan using any appropriate input portion, such as touching the screen 740. It will be understood, that the pre-operative plan file that is downloaded to the handheld device 712 can then be saved with the edits as the edited pre-operative plan and transmitted to the service provider 700 for appropriate edits to be re-reviewed or finalized, as discussed above. It will be understood, however, that the handheld device 712, which can include the appropriate program, can save the file in the appropriate format and transmit it back to the service provider 700.

Alternatively, or in addition to downloading the pre-operative plan file, the handheld device 712 can access the pre-operative plan which is stored in the main storage 704 associated with the service provider in block 606 and separate from the handheld device 712. If the handheld device 712 accesses the pre-operative plan on the main processor, memory 702, 704, the handheld device 712 need only display an image representing a portion of the file on the display screen 740. That is, the pre-operative plan and any edits or processing made to the pre-operative plan can be done solely or substantially by the main processor 702 that executes a program to manipulate and display the file. The main processor 702 and the main memory 704 need not be physically near or connected to the handheld device 712.

The handheld device 712 can be provided to display the image, such as an image of the bone for resection, for the surgeon 720. Therefore, the handheld device 712 may not be required to process the pre-operative plan file from the service provider 700, but only be provided to display the pre-operative plan file and receive and transmit input from the surgeon 720. Accordingly, even if the pre-operative plan is accessed from the service provider in block 606, the slide bars 520'c and 520'd can be displayed on the display 742 of the handheld device 712 for input by the surgeon 720. The inputs, however, can be directly transmitted to the main processor 702 for processing augmentation or editing of the file. This is in addition or alternative to augmenting or editing the file that has been downloaded to the handheld device 712 for re-transmission of the edited pre-operative plan to the service provider 700.

By only or substantially accessing the pre-operative plan file from the main processor/memory 702, 704 data transmission can be minimized from the main memory 704 or provider 700 to the handheld device 712 of the surgeon 720. Decreased data transmission can provide increased speed and decreased data usage costs or bottlenecks in a system. In addition, the handheld device 712 can be provided or include limited memory and processing capabilities when the pre-operative plan file is only accessed with the handheld 712 and only small amounts of information are transferred, for example, regarding slide bar location and smaller portions of an image file. Accordingly, it can be provided, that a complete or pre-operative plan is transmitted to the handheld device 712, processed completely on the handheld device 712, edited on the handheld device 712, saved and re-transmitted back to the service provider 700 or the handheld device 712 can only access the pre-operative plan file saved at the main memory 702 and transmit edits to the server.

Data transmission and processing can also be reduced by limiting or cropping the pre-operative plan data file. For example, as illustrated in FIG. 15, only a lateral and distal portion of the bone is illustrated on the display device or display screen 740 of the handheld device 712. It will be understood that an image file or image information can include the entire bone or other data saved in the image file. Accordingly, the image file can be cropped at the server or at the provider and only a portion of the image file transmitted to the handheld device 712. This can be done repeatedly for different portions of the image data to allow for smaller file packet size or file size for transmission to the handheld device 712. The cropping and compression of the data file can be done in substantially real-time by the server for a substantially seamless viewing and manipulation by the surgeon.

Even if the surgeon 720 accesses the data file on the main memory 704, the surgeon 720 can review the pre-operative plan block 140', as discussed above, and make a determination of whether the pre-operative plan is acceptable in block 620'. As discussed above, if the pre-operative plan is not acceptable, the NO path 622' can be followed to allow for surgeon edits in block 624'.

Further, regardless of the method of review of the pre-operative plan in block 140', the pre-operative plan can be determined to be acceptable in block 620' and follow the YES path 626'. When following the YES path 626', the implant can be designed and an alignment guide can be designed in blocks 150' and 160'.

The foregoing discussion discloses and describes merely exemplary arrangements of the present teachings. Furthermore, the mixing and matching of features, elements and/or functions between various embodiments is expressly contemplated herein, so that one of ordinary skill in the art would appreciate from this disclosure that features, elements and/or functions of one embodiment may be incorporated into another embodiment as appropriate, unless described otherwise above. Moreover, many modifications may be made to adapt a particular situation or material to the teachings of the invention without departing from the essential scope thereof. One skilled in the art will readily recognize from such discussion, and from the accompanying drawings and claims, that various changes, modifications and variations can be made therein without departing from the spirit and scope of the present teachings as defined in the following claims.

What is claimed is:

1. An orthopedic device manufacturing method comprising:

preparing pre-operatively a three-dimensional image of a patient's joint from imaging scans of the patient using computer modeling;

selecting pre-operatively a non-custom femoral implant closely matching the joint and having a plurality of planar surfaces corresponding to planned planar resections of a femoral bone of the joint, the planned resections including an anterior cut plane, anterior chamfer plane, distal cut plane, posterior chamfer plane and posterior cut plane;

manufacturing pre-operatively a customized femoral implant by a machining operation, the machining operation modifying at least six angles of the plurality of planar surfaces of the femoral implant to be patient-specific as determined from the three-dimensional image of the patient's joint, each patient-specific angle defined between a central plane perpendicular to a medial-lateral width of the femoral implant and lines connecting medial end points at medial edges between the planar resections and lateral points at lateral edges between the planar resections;

manufacturing a patient-specific femoral alignment guide;

coupling a removable tracking tag to the patient-specific femoral alignment guide for tracking the alignment guide from manufacture to surgery, the tracking tag including patient-specific information and configured to be removed prior to a corresponding surgical procedure; and preparing a surgical kit including the femoral implant and a patient-specific alignment guide for the surgical procedure.

2. The method of claim 1, wherein the six angles include three medial angles and three lateral angles of the implant.

3. The method of claim 1, further comprising machining at least three lengths of the implant to be patient specific, as determined from the three-dimensional image of the patient's joint.

4. The method of claim 3, wherein machining at least three lengths of the implant to be patient specific includes machining a medial condyle width of the femoral implant.

5. The method of claim 3, wherein machining at least three lengths of the implant to be patient specific includes machining a lateral condyle width of the femoral implant.

6. The method of claim 3, wherein machining at least three lengths of the implant to be patient specific includes machining a notch height width of the femoral implant.

7. The method of claim 1, further comprising tracking the patient information from manufacture to implant procedure.

8. The method of claim 1, wherein the surgical kit includes additional surgeon-selected instruments.

9. The method of claim 1, wherein the surgical kit is designed to be disposable.

10. The method of claim 1, wherein the tracking tag is inserted in a pocket formed in an extension of the alignment guide.

11. The method of claim 10, wherein the extension is frangible.

* * * * *